United States Patent
Hirotsuka et al.

(10) Patent No.: US 8,618,312 B2
(45) Date of Patent: Dec. 31, 2013

(54) METHOD OF PRODUCING BICYCLO[3.1.0] HEXANE DERIVATIVE USING ENZYME

(75) Inventors: Mitsuaki Hirotsuka, Tokyo (JP); Joji Sasaki, Tokyo (JP); Hiroaki Kamiyama, Tokyo (JP); Motoko Oshida, Tokyo (JP); Takaaki Ishii, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 446 days.

(21) Appl. No.: 12/950,609

(22) Filed: Nov. 19, 2010

(65) Prior Publication Data

US 2011/0065934 A1  Mar. 17, 2011

Related U.S. Application Data

(63) Continuation-in-part of application No. PCT/JP2009/059156, filed on May 19, 2009.

(30) Foreign Application Priority Data

May 21, 2008 (JP) ................................. 2008-133056

(51) Int. Cl.
C07D 327/04 (2006.01)
C07D 317/72 (2006.01)

(52) U.S. Cl.
USPC ........................................... 549/33; 549/342

(58) Field of Classification Search
USPC ........................................ 549/33.6, 342, 336
See application file for complete search history.

(56) References Cited

U.S. PATENT DOCUMENTS

| | | | | |
|---|---|---|---|---|
| 6,160,009 | A * | 12/2000 | Massey et al. | 514/510 |
| 6,333,428 | B1 | 12/2001 | Nakazato et al. | |
| 6,407,284 | B1 | 6/2002 | Kudo et al. | |
| 6,825,375 | B2 | 11/2004 | Nakazato et al. | |
| 7,786,364 | B2 * | 8/2010 | Natali | 84/412 |
| 2004/0209931 | A1 | 10/2004 | Holla et al. | |
| 2007/0112030 | A1 | 5/2007 | Hartner et al. | |

FOREIGN PATENT DOCUMENTS

| | | |
|---|---|---|
| JP | 63-5056 A | 1/1988 |
| JP | 09-052887 A | 2/1997 |
| JP | 2000-300285 A | 10/2000 |
| JP | 2006-519001 A | 8/2006 |
| JP | 2007-513070 A | 5/2007 |
| WO | 2005/047215 A2 | 5/2005 |

OTHER PUBLICATIONS

Schoepp, D.et al., "Pharmacological and functional characteristics of metabotropic excitatory amino acid receptors", *TiPS*, vol. 11, Dec. 1990, pp. 508-515.

McDonald, J. W. et al., "Physiological and pathophysiological roles of excitatory amino acids during central nervous system development", *Brain Research Reviews*, Jan. 1990. pp. 41-70.

Nakazato, A. et al., "Synthesis, SARs, and Pharmacological Characterization of 2-Amino-3 or 6-fluorobicyclo[3.1.0]hexane-2,6-dicarboxylic Acid Derivatives as Potent, Selective, and Orally Active Group II Metabotropic Glutamate Receptor Agonists", *Journal of Medical Chemistry*, 2000, vol. 43. pp. 4893-4909.

Yasuda, N., Tan. L. et al., "Stereoselective Syntheses of Highly Functionalized Bicyclo[3.1.0]hexanes: A General Methodology for the Synthesis of Potent and Selective mGluR2/3 Agonists", *Journal of Organic Chemistry*, 2005, vol. 70, pp. 8027-8034.

Korach, M. et al., "Dihydroxycyclopentene", *Organic Syntheses*, 1962, vol. 42, pp. 50-54.

Frohner, W. et al; "Regiospecific Synthesis of Mono-N-substituted Indolopyrroloacarbazoles",*Organic Letters*, 2005, vol. 7, No. 21, pp. 4573-4576.

Mikame, D. et al., "Mn-Salen Catalyzed Asymmetric Epoxidation of 1,3-Cycloalkadiences and Dialkylsubstituted Z-Olefins", *Synlett*, 1995, vol. 8. pp. 872-873.

Zaidlewicz M. et al., "Syntheses with Organoboranes. VI. Kinetic Resolution of Vinylic Epoxides by the Reduction with Chiral Dialkylboranes", *Tetrahedron Letters*, 1996, vol. 37, No. 39. pp. 7129-7135.

Lau, R. M. et al., "Lipase-Catalyzed Reactions in Ionic Liquids", *Organic Letters*, 2000, vol. 2, No. 26, pp. 4189-4191. Zhang F. et al., "Enantioselective Preparation of Ring-Fused 1-Fluorocyclopropane-1-carboxylate Derivatives: En Route to mGluR 2 Receptor Agonist MGS0028", *Organic Letters*, 2004, Vo. 6. No. 21, pp. 3775-3777.

Korach, M. et al., "Synthesis and Reactions of 3,4-Epoxycyclopentene", *Journal of the American Chemical Society*, 1960, vol. 82, No. 16, pp. 4327-4330.

International Search Report dated Jul. 7, 2009 issued in corresponding PCT/JP2009/059156.

* cited by examiner

Primary Examiner — Andrew D Kosar
Assistant Examiner — Raymond Covington
(74) Attorney, Agent, or Firm — Sughrue Mion, PLLC

(57) ABSTRACT

Production of a bicyclo[3.1.0]hexane derivative, useful as a metabotropic glutamate receptor modulator, becomes possible by a production method that includes converting a compound represented by Formula (II) into a compound represented by Formula (III) by reaction with an acyl group donor in the presence of a microorganism-derived enzyme, without using an expensive optically active trans hydroxy ester as a starting material and without employing a fluorination reaction requiring an ultralow temperature reaction. Furthermore, since asymmetric synthesis can be carried out in a stage closer to the final product, the production method is useful as a production method that can mass produce a bicyclo[3.1.0] hexane derivative.

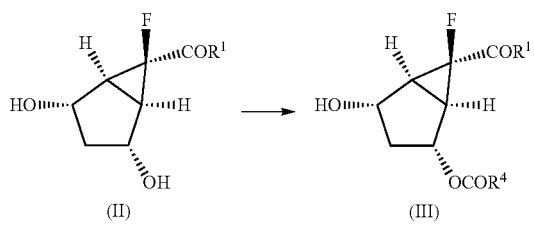

23 Claims, No Drawings

METHOD OF PRODUCING BICYCLO[3.1.0] HEXANE DERIVATIVE USING ENZYME

CROSS-REFERENCE TO RELATED APPLICATIONS

This application is a Continuation-In-Part of PCT international application No. PCT/JP2009/059,156 filed May 19, 2009 and designating the U.S., which claims priority from Japanese patent application No. 2008-133,056 filed May 21, 2008, the contents of which are incorporated hereinto by reference.

BACKGROUND

1. Technical Field

The present invention relates to a method for producing a bicyclo[3.1.0]hexane derivative, which is a metabotropic glutamate receptor modulator useful as a pharmaceutical. Furthermore, the present invention relates to a novel intermediate compound produced in the above production process.

2. Related Art

An excitatory amino acid such as glutamic acid modulates various physiological processes such as long term potentiation (learning and memory), synaptic plasticity development, motor control, respiration, cardiovascular modulation, and perception in the central nervous system (CNS) of a mammal.

Glutamic acid acts via at least two different classes of receptor. One of the classes is an ionotropic glutamate (iGlu) receptor, which functions as a ligand-gated ion channel. The second class is a G protein- or second messenger-binding 'metabotropic' glutamate (mGluR) receptor. It appears that receptors of either class mediate normal synaptic transmission in accordance with an excitatory pathway. It also appears that they are involved in modification of synaptic binding from the development stage throughout the lifetime (ref. Schoepp, Bockaert, and Sladeczek, Trends in Pharmacol. Sci., 11, 508 (1990), and McDonald and Johnston, Brain Research Reviews, 15, 41 (1990)).

Various bicyclo[3.1.0]hexane derivative compounds are recognized as mGluR modulators. mGluR modulators are useful for the prevention or treatment of nervous system diseases such as schizophrenia, anxiety disorder, depression, bipolar disorder, epilepsy, drug dependence disease, cognitive disorder, Alzheimer's disease, Huntington's chorea, Parkinson's disease, dyskinesia accompanied by muscle rigidity, cerebral ischemic, encephalopathy, or head injury.

For example, as mGluR agonists, a 2-amino-6-fluorobicyclo[3.1.0]hexane derivative represented by Formula (IA) below and a pharmaceutically acceptable salt thereof have been disclosed (ref. U.S. Pat. No. 6,333,428).

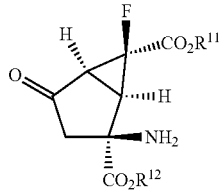
(IA)

In the formula, $R^{11}$ and $R^{12}$ are independently selected from the group consisting of
(1) hydrogen;
(2) a $C_{1-10}$ alkyl group;
(3) a $C_{3-8}$ cycloalkyl group; and
(4) a $C_{3-8}$ cycloalkyl-$C_{1-5}$ alkyl group. U.S. Pat. No. 6,333,428 above states that the compound of the invention may be a racemic modification or an enantiomer.

Other than U.S. Pat. No. 6,333,428 above, there are reports on methods for preparing mGluR modulators and intermediates therefor at a laboratory scale (ref. U.S. Pat. No. 6,825,375, and Nakazato et al., J. Med. Chem., 43, 4893 (2000)).

Furthermore, there are also reports on a production method that can cope with production of an mGluR modulator and an intermediate therefor on a larger scale (ref. WO05/47215, and Yasuda et al., J. Org. Chem., 70, 8027 (2005)).

SUMMARY

The production methods disclosed in WO05/47215 and Yasuda et al., J. Org. Chem., 70, 8027 (2005) have the problem that a fluorination reaction in the first step requires ultralow temperature conditions (−65° C. or less), which are not suitable for mass production, and an expensive fluorinating agent such as N-fluorobenzenesulfonimide. Furthermore, in this production method, an optically active trans hydroxy ester is used as a starting material, the synthesis thereof requires an expensive reagent, and it is not easy to control the large heat of reaction, which are disadvantages for mass production.

Since the mGluR modulators disclosed in U.S. Pat. No. 6,333,428 are useful as therapeutic drugs, with regard to a method for producing these compounds, there is a need for development of a method that enables easy scaling up, can use a reagent that is cost-effective and safe, and can thereby be put into practice for mass production.

As a result of an intensive investigation by the inventors of the present application, a novel method and a novel intermediate compound have been found for producing a more practical enantiomerically pure bicyclo[3.1.0]hexane derivative by using a starting material that already contains a fluorine atom to thus avoid a fluorination reaction and by carrying out an asymmetric acylation reaction using an enzyme to thus avoid use of an optically active trans hydroxy ester.

That is, according to the present invention, there is provided a method for producing a bicyclo[3.1.0]hexane derivative represented by Formula (I) and a salt thereof

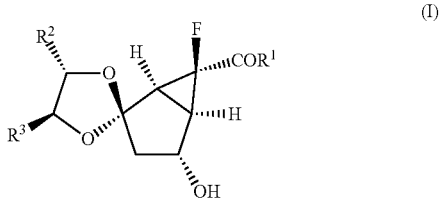
(I)

(in Formula (I), $R^1$ is
(1) —OH,
(2) —O—$R^a$, or
(3) —$NR^bR^c$,
$R^a$ is a $C_{1-6}$ alkyl group or a $C_{3-8}$ cycloalkyl group (the $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (the $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups), or $R^b$ and $R^c$ are bonded to each other and, together with the adjacent nitrogen atom, form a 4- to 7-membered saturated heterocycle (the saturated heterocycle being unsubstituted or substituted with a hydroxy group, a $C_{1-6}$ alkyl group, or a $C_{1-6}$ alkoxy group), $R^2$ and $R^3$ are identical or different and are each hydrogen, a $C_{1-6}$ alkyl group, a $C_{3-8}$ cycloalkyl group, or a —$(CH_2)_m$-phenyl group, and m is 0, 1, or 2), the method including (A) converting a compound represented by Formula (II) into a compound represented by Formula (III)

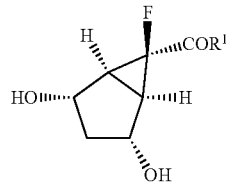
(II)

($R^1$ in Formula (II) is as defined in Formula (I))

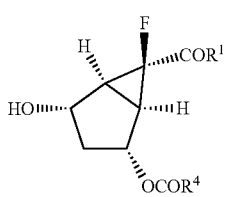
(III)

(in Formula (III), $R^1$ is as defined in Formula (I), $R^4$ is hydrogen, a $C_{1-6}$ alkyl group, a $C_{3-8}$ cycloalkyl group, or a —$(CH_2)_n$-phenyl group (the $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups), and n is 0, 1, or 2), (B) converting the compound represented by Formula (III) into a compound represented by Formula (IV)

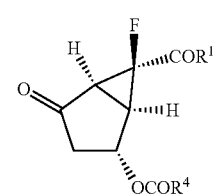
(IV)

($R^1$ and $R^4$ in Formula (IV) are as defined in Formula (I) and Formula (III)), (C) reacting the compound represented by Formula (IV) with a compound represented by Formula (V) to obtain a compound represented by Formula (VI)

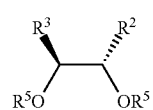
(V)

(in Formula (V), $R^2$ and $R^3$ are as defined in Formula (I), $R^5$ is hydrogen or Si—$(R^5)(R^7)(R^8)$, $R^6$, $R^7$ and $R^8$ are identical or different and are each a $C_{1-6}$ alkyl group or a phenyl group)

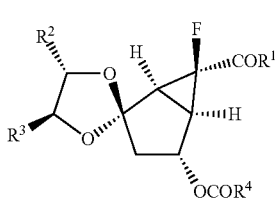
(VI)

($R^1$, $R^2$, and $R^3$ in Formula (VI) are as defined in Formula (I) and $R^4$ is as defined in Formula (III)), and (D) converting the compound represented by Formula (VI) into the compound represented by Formula (I).

Furthermore, according to the present invention, there is provided a production method that includes converting a compound represented by Formula (II) into the compound represented by Formula (III)

Moreover, according to the present invention, there is provided a method for producing a compound represented by Formula (VII) and a salt thereof

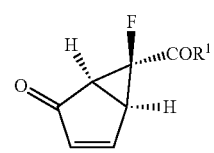
(VII)

(in Formula (VII), $R^1$ is (1) —OH, (2) —O—$R^a$, or (3) —$NR^bR^c$, $R^a$ is a $C_{1-6}$ alkyl group or a $C_{3-9}$ cycloalkyl group (the $C_{1-6}$ alkyl group or $C_{3-6}$ cycloalkyl group being unsubstituted or substituted with one or more $C_{1-6}$ alkoxy groups, hydroxy groups, halogens, aryl groups, or heteroaryl groups), $R^b$ and $R^c$ are identical or different and are each hydrogen, a halogen, a $C_{1-6}$ alkyl group, or a $C_{3-8}$ cycloalkyl group (the $C_{1-6}$ alkyl group or $C_{3-6}$ cycloalkyl group being unsubstituted or substituted with one or more hydroxy groups, alkoxy groups, aryl groups, or heteroaryl groups), or $R^b$ and are bonded to each other and, together with the adjacent nitrogen atom, form a 4- to 7-membered saturated heterocycle (the saturated heterocycle being unsubstituted or substituted with a hydroxy group, a $C_{1-6}$ alkyl group, or a $C_{1-6}$ alkoxy group)), the method including (A) converting a compound represented by Formula (II) into a compound represented by Formula (III), (B) converting the compound represented by Formula (III) into a compound represented by Formula (IV), and (C) converting the compound represented by Formula (IV) into the compound represented by Formula (VII).

Furthermore, according to the present invention, there is provided a method for producing a compound represented by Formula (II) and a salt thereof, the method including (A) reacting a compound represented by Formula (VIII) with a compound represented by Formula (IX) to obtain a mixture formed from a compound represented by Formula (Xa) and a compound represented by Formula (Xb)

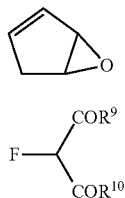
(VIII)

(IX)

(in Formula (IX), $R^9$ and $R^{10}$ are identical or different and are each (1) —OH, (2) —O—$R^a$, or (3) —$NR^bR^c$, $R^a$ is a $C_{1-6}$ alkyl group or a $C_{3-6}$ cycloalkyl group (the $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups), $R^b$ and $R^c$ are identical or different and are each hydrogen, a halogen, a $C_{1-6}$ alkyl group, or a $C_{3-8}$ cycloalkyl group (the $C_{1-6}$ alkyl group or $C_{3-8}$ cycloalkyl group being unsubstituted or substituted with one or more hydroxy groups, $C_{2-6}$ alkoxy groups, aryl groups, or heteroaryl groups), or $R^b$ and $R^c$ are bonded to each other and, together with the adjacent nitrogen atom, form a 4- to 7-membered saturated heterocycle (the saturated heterocycle being unsubstituted or substituted with a hydroxy group, a $C_{1-6}$ alkyl group, or a $C_{1-6}$ alkoxy group))

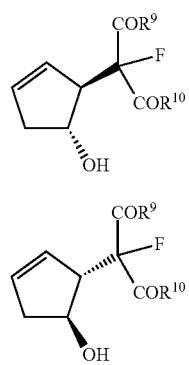
(Xa)

(Xb)

($R^9$ and $R^{10}$ in Formulae (Xa) and (Xb) are as defined in Formula (IX)), (B) converting a mixture formed from the compound represented by Formula (Xa) and the compound represented by Formula (Xb) into a mixture formed from a compound represented by Formula (XIa) and a compound represented by Formula (XIb)

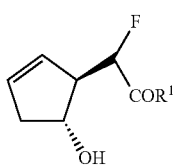
(XIa)

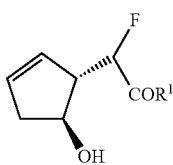
(XIb)

($R^1$ in Formulae (XIa) and (XIb) is as defined in Formula (II)), (C) converting a mixture formed from the compound represented by Formula (XIa) and the compound represented by Formula (XIb) into a mixture formed from a compound represented by Formula (XIIa) and a compound represented by Formula (XIIb)

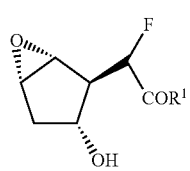
(XIIa)

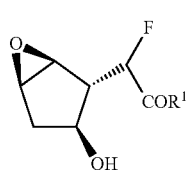
(XIIb)

($R^1$ in Formulae (XIIa) and (XIIb) is as defined in Formula (II)), and (D) converting a mixture formed from the compound represented by Formula (XIIa) and the compound represented by Formula (XIIb) into the compound represented by Formula (II).

Moreover, according to the present invention, there is provided a production method that includes reacting a compound represented by Formula (VIII) with a compound represented by Formula (IX) so as to convert them into a mixture formed from the compound represented by Formula (Xa) and the compound represented by Formula (Xb).

Furthermore, according to the present invention, there are provided compounds represented by Formulae (II), (III), (IV), and (VI) and salts thereof.

Moreover, according to the present invention, there is provided a method for producing a compound represented by Formula (III) and a salt thereof, the method including

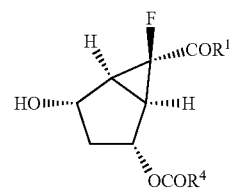
(III)

converting a compound represented by Formula (XIII) into the compound represented by Formula (III).

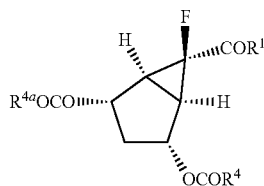

(XIII)

(In Formula (XIII), R⁴ and R⁴ª are identical or different and are each hydrogen, a $C_{1-6}$ alkyl group, a $C_{3-8}$ cycloalkyl group, or a —$(CH_2)_n$-phenyl group (the $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups) and n is 0, 1, or 2.)

Compounds represented by Formulae (I), (II), (III), (IV), (VI), (VII), (Xa), (Xb), (XIa), (XIb), (XIIa), and (XIIb) and salts thereof are intermediates prepared in the synthesis of bicyclo[3.1.0]hexane derivative mGluR modulators represented by Formula (IA) and salts thereof. A compound represented by Formula (IA) and a salt thereof may be produced by a literature method from a compound represented by Formula (I) or a compound represented by Formula (VII) and a salt thereof (ref. WO05/47215, McDonald and Johnston, Brain Research Reviews, 15, 41 (1990) and Nakazato et al., J. Med. Chem., 43, 4893 (2000)).

In accordance with use of the production method of the present invention, it becomes possible to produce a bicyclo [3.1.0]hexane derivative mGluR modulator without using an expensive optically active trans hydroxy ester as a starting material. That is, a compound of Formula (VIII), which is a starting material, may be an optically active substance or a racemic modification, and an optically inactive intermediate meso-diol (a compound of Formula (II)) can be produced from this starting material. It has been found that, by an asymmetric acylation method employing an enzymic meso trick method utilizing a specific microorganism-derived enzyme, a compound of Formula (III) can be produced from the compound of Formula (II) above, and asymmetric synthesis in a stage closer to a final product becomes possible.

Moreover, since it is possible to use a fluorine atom-containing starting material (compound of Formula IX) in the production method of the present application, it becomes possible to produce a bicyclo[3.1.0]hexane derivative mGluR modulator without going through a fluorination reaction, in which an ultralow temperature reaction is required.

DETAILED DESCRIPTION

The '$C_{1-6}$ alkyl group' denotes a straight-chain or branched alkyl group having 1 to 6 carbon atoms, and examples thereof include methyl, ethyl, n-propyl, isopropyl, n-butyl, isobutyl, sec-butyl, tert-butyl, n-pentyl, isopentyl, neopentyl, and n-hexyl groups.

The '$C_{3-8}$ cycloalkyl group' denotes a cyclic alkyl group having 3 to 8 carbon atoms, and examples thereof include cyclopropyl, cyclobutyl, cyclopentyl, cyclohexyl, cycloheptyl, and cyclooctyl groups.

The '$C_{1-6}$ alkoxy group' denotes a straight-chain or branched alkoxy group having 1 to 6 carbon atoms, and examples thereof include methoxy, ethoxy, n-propoxy, iso-propoxy, n-butoxy, isobutoxy, sec-butoxy, tert-butoxy, n-pentyloxy, isopentyloxy, neopentyloxy, and n-hexyloxy groups.

The 'halogen' is fluorine, chlorine, and bromine.

The 'aryl group' denotes an aromatic hydrocarbon substituent and may be monocyclic or polycyclic (preferably monocyclic to tricyclic), and the rings in the polycycle may or may not be fused. Examples thereof include phenyl, naphthyl, and biphenyl groups.

The 'heteroaryl group' denotes an aromatic ring having at least one heteroatom (nitrogen, oxygen, or sulfur) in the ring skeleton. The heteroaryl group may be monocyclic or polycyclic (preferably monocyclic to tricyclic), and the rings in the polycycle may or may not be fused. Examples thereof include groups such as pyrrole, pyrazole, imidazole, pyridine, pyrazine, pyrimidine, furan, pyran, oxazole, isooxazole, purine, benzimidazole, quinoline, isoquinoline, and indole. When the heteroaryl group defined here is substituted, the substituent may be bonded to a carbon atom forming the ring of the heteroaryl group or may be bonded to a nitrogen atom forming the ring, and has a valence that enables substitution. The substituent is preferably bonded to a carbon atom forming the ring.

The 'bonding to each other and, together with the adjacent nitrogen atom, forming a 4- to 7-membered saturated heterocycle' denotes groups such as azetidinyl, pyrrolidinyl, piperidinyl, and azepanyl.

The 'microorganism-derived enzyme' denotes for example an enzyme derived from a microorganism such as a fungus or a bacterium, and may be obtained from an extract in which such a microorganism is ground or a culture supernatant of such a microorganism. As the enzyme, there can be cited a lipase, an acylase, and the like; it is not limited to one type, and a plurality of enzymes may be present simultaneously. Examples of the fungus include the *Candida* genus, the *Aspergillus* genus, the *Thermomyces* genus, the *Penicillium* genus, the *Geotrichum* genus, the *Galactomyces* genus, and the *Humicola* genus. Examples of the bacterium include the *Burkholderia* genus.

A 'support' is not particularly limited as long as it is a support that can immobilize an enzyme; examples thereof include Celite (trade name), which is a diatomaceous earth calcined together with sodium carbonate, and Toyonite (trade name), which is a porous ceramic-based support obtained by hydrothermally processing a kaolin mineral under hydrochloric acid-acidified conditions, then granulating, and calcining it. It is possible to easily modify the surface of Toyonite particles with various organic functional groups. By changing the type of organic functional group (methacryloyloxy group, phenylamine group, amino group, and the like) of a coupling agent used for modification of the surface of Toyonite, various types of enzyme may be more selectively immobilized. By immobilizing an enzyme on a simple substance such as Celite or Toyonite, the stability, reaction activity, and the like of the enzyme are increased.

The 'salt' includes, for example, a salt with an inorganic acid such as sulfuric acid, hydrochloric acid, hydrobromic acid, phosphoric acid, or nitric acid, a salt with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid, or naphthalene-2-sulfonic acid, a salt with one or more types of metal ions such as lithium ion, sodium ion, potassium ion, calcium ion, magnesium ion, zinc ion, or aluminum ion, and a salt with an amine such as ammonia, arginine, lysine, piperazine, choline, diethylamine, 4-phenylcyclohexylamine, 2-aminoethanol, or benzathine.

'Enantiomerically pure' denotes that a target enantiomer is present in at least 50% e.e. (enantiomeric excess) relative to an untargeted enantiomer, preferably at least 80% e.e., and yet more preferably at least 90% e.e.

A bicyclo[3.1.0]hexane derivative mGluR modulator represented by Formula (IA) and a salt thereof may be produced from a compound represented by Formula (I) by a method known in the art. For example, WO05/47215 describes a method for synthesizing a compound represented by Formula (IA) using a compound represented by Formula (I).

A preferred embodiment of the method for producing a compound represented by Formula (I) in the present invention is use of a compound of Formula (II) as a starting material. It is preferable that $R^1$ be a methoxy group, an ethoxy group, or a benzyloxy group. It is more preferable that $R^1$ be a methoxy group or an ethoxy group, and it is yet more preferable that $R^1$ be a methoxy group.

In a preferred embodiment of the method for producing a compound represented by Formula (I) in the present invention, $R^2$ and $R^3$ are selected from the group consisting of a methyl group and a phenyl group. Furthermore, it is preferable that $R^2$ and $R^3$ be the same substituents, and it is more preferable that $R^2$ and $R^3$ be phenyl groups.

In a preferred embodiment of the method for producing a compound represented by Formula (I) in the present invention, $R^4$ is a methyl group.

In a preferred embodiment of the method for producing a compound represented by Formula (I) in the present invention, the $R^5$s are hydrogen and a trimethylsilyl group.

A bicyclo[3.1.0]hexane derivative mGluR modulator represented by Formula (IA) and a salt thereof may be produced from a compound of Formula (VII) above by a method known in the art. For example, Nakazato et al., J. Med, Chem., 43, 4893-4909 (2000) describes a method for synthesizing a compound represented by Formula (IA) using a compound represented by Formula (VII).

A preferred embodiment of the method for producing a compound represented by Formula (VII) in the present invention employs a compound represented by Formula (II) as a starting material. It is preferable that $R^1$ be a methoxy group, an ethoxy group, or a benzyloxy group, it is more preferable that $R^1$ be a methoxy group or an ethoxy group, and it is yet more preferable that $R^1$ be a methoxy group.

In a preferred embodiment of the method for producing a compound represented by Formula (VII) in the present invention, the $R^4$ group is a methyl group.

Bicyclo[3.1.0]hexane derivatives represented by Formula (I) and Formula (VII) may be produced from a [3.1.0]hexane derivative represented by Formula (III) and a salt thereof using the above-mentioned method.

A preferred embodiment of the method for producing a compound represented by Formula (III) in the present invention employs a compound represented by Formula (II) as a starting material. It is preferable that $R^1$ be a methoxy group, an ethoxy group, or a benzyloxy group, it is more preferable that $R^1$ be a methoxy group or an ethoxy group, and it is yet more preferable that $R^1$ be a methoxy group.

In a preferred embodiment of the method for producing a compound represented by Formula (III) in the present invention, $R^4$ is a methyl group, an ethyl group, a propyl group, a butyl group, a heptyl group, a monochloromethyl group, or a phenyl group. It is yet more preferable that $R^4$ be a methyl group.

A preferred embodiment of the method for producing a compound represented by Formula (II) in the present invention employs compounds represented by Formula (VIII) and Formula (IX) as starting materials. It is preferable that $R^1$ be a methoxy group, an ethoxy group, or a benzyloxy group, it is more preferable that $R^1$ be a methoxy group or an ethoxy group, and it is yet more preferable that $R^1$ be a methoxy group. It is preferable that $R^9$ and $R^{10}$ be methoxy groups, ethoxy groups, or benzyloxy groups. It is preferable that $R^9$ and $R^{10}$ be the same substituents, and it is more preferable that $R^9$ and $R^{10}$ be methoxy groups.

One embodiment of the production method of the present invention is shown in Scheme 1 and Scheme 2 below.

Scheme 1

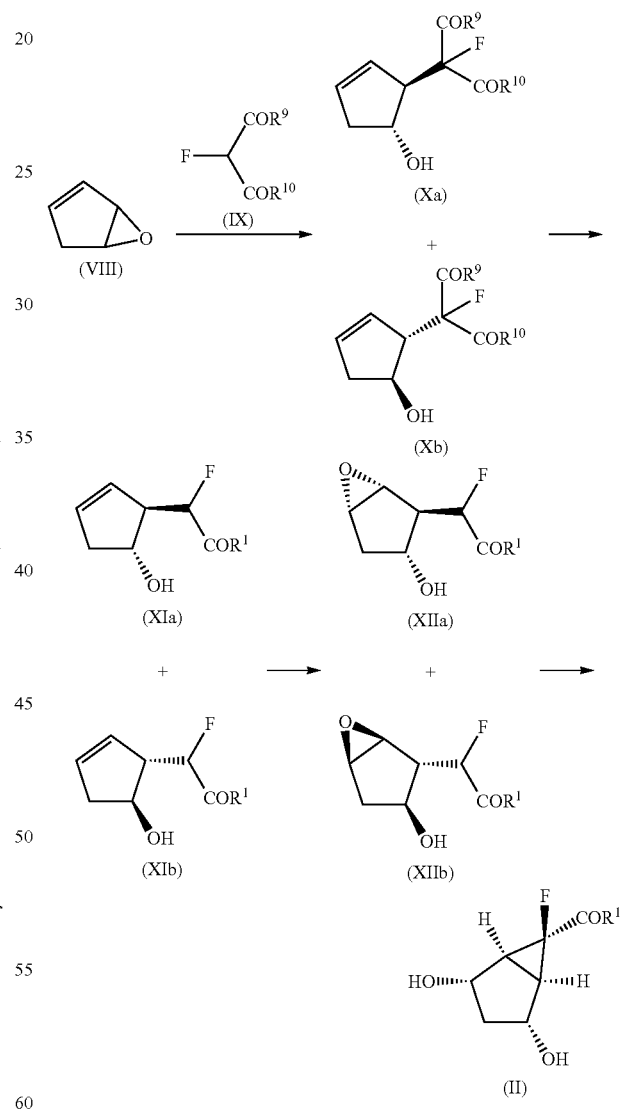

(Scheme 1)

In the formulae, $R^1$, $R^9$, and $R^{10}$ are as defined above.

The compound represented by Formula (VIII) may be an optically active substance or an optically inactive substance. The compound represented by Formula (VIII) may be synthesized by oxidizing cyclopentadiene using, for example, a peracid such as peracetic acid (J. Am. Chem. Soc., 82, 4328

(1960), Org. Synth., 42, 50 (1962)., Org. Lett., 7, 4573 (2005)). Furthermore, an optically active substance of the compound represented by Formula (VIII) may be synthesized by asymmetric oxidation of cyclopentadiene in the presence of, for example, a metal catalyst (Synlett, 827 (1995), Tetrahedron Letters, 37, 7131 (1996), JP-A-09-052887).

By reacting a compound represented by Formula (VIII) and a compound represented by Formula (IX) in the presence of a base, a mixture of a compound represented by Formula (Xa) and a compound represented by Formula (Xb) is obtained.

Examples of the base used in the reaction include an alkali metal alkoxide such as sodium methoxide, sodium ethoxide, or potassium tert-butoxide, an alkali metal hydride such as sodium hydride or potassium hydride, an alkali metal hydroxide such as sodium hydroxide or potassium hydroxide, an organic amine such as 1,8-diazabicyclo[5.4.0]-7-undecene, and a metal amide such as lithium diisopropylamide or lithium hexamethyldisilazide; it is preferable to use an alkali metal alkoxide, it is more preferable to use an alkali metal methoxide or an alkali metal ethoxide, and it is yet more preferable to use sodium methoxide.

The amount of base used is not particularly limited as long as it is an amount that does not inhibit the reaction and does not cause a side reaction, but it may usually be used in the range of 0.5 to 5 molar equivalents relative to the compound represented by Formula (VIII), preferably in the range of 1 to 3 molar equivalents, and more preferably in the range of 1 to 2 molar equivalents.

The amount of compound represented by Formula (IX) used is not particularly limited as long as it is an amount that does not inhibit the reaction and does not cause a side reaction, but it may usually be used in the range of 0.5 to 5 molar equivalents relative to the compound represented by Formula (VIII), preferably in the range of 1 to 3 molar equivalents, and more preferably in the range of 1 to 2.5 molar equivalents.

A solvent used in the reaction is not particularly limited as long as it is stable under relevant reaction conditions and does not inhibit a target reaction, but since the yield of the mixture of a compound represented by Formula (Xa) and a compound represented by Formula (Xb), which are products, depends on the type of solvent, it is preferable to use an alcohol, and more preferably methanol, as a solvent.

The amount of reaction solvent used is usually 1 to 100 times by mass relative to the compound represented by Formula (VIII), and preferably in the range of 5 to 30 times by mass.

The reaction temperature may be usually from −80° C. to the boiling point of the solvent used, is preferably in the range of −20° C. to 60° C., and is more preferably in the range of 20° C. to 40° C.

Subsequently, by heating the mixture of a compound represented by Formula (Xa) and a compound represented by Formula (Xb) in the presence of an additive, a mixture of a compound represented by Formula (XIa) and a compound represented by Formula (XIb) is obtained.

A solvent used in the reaction is not particularly limited as long as it is stable under relevant reaction conditions and does not inhibit the target reaction. Since the yield of the mixture of a compound represented by Formula (XIa) and a compound represented by Formula (XIb), which are products, depends on the type of solvent, it is preferable to use a mixture of water and a polar organic solvent, more preferably water and dimethyl sulfoxide, and yet more preferably water and dimethyl sulfoxide at a ratio in the range of 0:5 to 1:5.

The amount of reaction solvent used may be usually 1 to 100 times by mass relative to the mixture of a compound represented by Formula (Xa) and a compound represented by Formula (Xb), is preferably in the range of 1 to 20 times by mass, and is more preferably in the range of 1 to 10 times by mass.

The reaction temperature may usually be from 80° C. to 200° C., but is preferably in the range of 90° C. to 160° C., and more preferably in the range of 100° C. to 130° C.

When the reaction temperature exceeds the boiling point of the solvent used, the reaction may be carried out in a pressure-resistant container such as an autoclave.

Furthermore, the present reaction is accelerated by addition of the additive; examples of the additive that can be used include a salt, preferably an alkali metal halide salt such as lithium chloride, sodium chloride, potassium chloride, lithium bromide, sodium bromide, potassium bromide, lithium iodide, sodium iodide, or potassium iodide, an alkali metal cyanide salt such as sodium cyanide, a quaternary ammonium salt such as tetra-n-butylammonium chloride, tetra-n-butylammonium bromide, or tetra-n-butylammonium iodide, an organic amine salt such as triethylamine hydrochloride, or a mixture thereof. It is also possible to use an alkali metal halide salt such as sodium chloride and an acid such as acetic acid in combination.

The amount of additive used is not particularly limited as long as it is an amount that does not inhibit the reaction and does not cause a side reaction, but it is usually in the range of 0.5 to 5 molar equivalents relative to the mixture of a compound represented by Formula (Xa) and a compound represented by Formula (Xb), preferably in the range of 1 to 4 molar equivalents, and more preferably in the range of 1 to 3 molar equivalents, Subsequently, the mixture of a compound represented by Formula (XIa) and a compound represented by Formula (XIb) is oxidized in the presence of an additive, thus giving a mixture of a compound represented by Formula (XIIa) and a compound represented by Formula (XIIb).

The present reaction proceeds by adding an oxidizing agent such as tert-butyl hydroperoxide in the presence of a catalyst such as vanadyl acetylacetonate ($VO(acac)_2$).

A solvent used in the reaction is not particularly limited as long as it is stable under relevant reaction conditions and does not inhibit the target reaction. Since the yield of the mixture of a compound represented by Formula (XIIa) and a compound represented by Formula (XIIb), which are products, depends on the type of solvent, it is preferable to use an aromatic hydrocarbon or a halogenated hydrocarbon, more preferably chlorobenzene or toluene, and yet more preferably chlorobenzene.

The amount of reaction solvent used may be 3 to 100 times by mass relative to the mixture of a compound represented by Formula (XIa) and a compound represented by Formula (XIb), preferably 3 to 20 times by mass, and is more preferably 5 to 10 times by mass.

The reaction temperature may usually be 0° C. to 100° C., but is preferably in the range of 30° C. to 80° C., and more preferably 50° C. to 60° C., The amount of oxidizing agent used is not particularly limited as long as it is an amount that does not inhibit the reaction and does not cause a side reaction, but it may usually be used at 1 to 3 molar equivalents relative to the mixture of a compound represented by Formula (XIa) and a compound represented by Formula (XIb), and is preferably in the range of 1 to 2 molar equivalents.

The amount of catalyst used is not particularly limited as long as it is an amount that does not inhibit the reaction and does not cause a side reaction, but it may usually be used at 0.01 to 1 molar equivalents relative to the mixture of a compound represented by Formula (XIa) and a compound represented by Formula (XIb), and is preferably in the range of 0.2 to 0.5 molar equivalents.

Furthermore, epoxidetion of the mixture of a compound represented by Formula (XIa) and a compound represented by Formula (XIb) may also be carried out by reacting with a halogenating agent such as N-bromosuccinimide or N-iodosuccinimide in an appropriate solvent (for example, a mixture of dimethyl sulfoxide and water) to convert them into halohydrin derivatives, and then treating with a base such as 1,8-diazabicyclo[5.4.0]-7-undecene.

Subsequently, by subjecting the mixture of a compound represented by Formula (XIIa) and a compound represented by Formula (XIIb) to an intramolecular cyclopropanation accompanied by epoxide ring opening, a compound represented by Formula (II) is obtained.

This reaction proceeds by adding a base in the presence of a Lewis acid.

In a preferred embodiment, first, the mixture of a compound represented by Formula (XIIa) and a compound represented by Formula (XIIb) is treated with a Lewis acid, and a base is then added. The compound represented by Formula (II) is obtained as the desired stereoisomer.

Examples of the Lewis acid include $R_3Al$, $R_2AlX$, $RAlX_2$, $Al(OR)_3$, $Ti(OR)_4$, $RTi(OR)_3$, $R_2Ti(OR)_2$, a $BF_3$ ether complex, $Et_2Zn$, and $Sc(OTf)_3$; it is preferably $Et_3Al$, $Al(OiPr)_3$, $Ti(OiPr)_4$, a $BF_3$ ether complex, $Et_2Zn$, and $Sc(OTf)_3$, more preferably $Et_3Al$, $Et_1AlCl$, and $Et_2Zn$, and yet more preferably $Et_3Al$. Here, X is a halogen or an inorganic radical, and the Rs are independently hydrocarbon groups.

The amount of Lewis acid used is not particularly limited as long as it is an amount that does not inhibit the reaction and does not cause a side reaction, but it may usually be used in the range of 1 to 5 molar equivalents relative to the mixture of a compound represented by Formula (XIIa) and a compound represented by Formula (XIIb), preferably in the range of 1.5 to 3 molar equivalents, and more preferably in the range of 2 to 2.5 molar equivalents.

Examples of the base include lithium hexamethyldisilazide and lithium diisopropylamide, and it is preferably lithium hexamethyldisilazide.

The amount of base used is not particularly limited as long as it is an amount that does not inhibit the reaction and does not cause a side reaction, but it may usually be used in the range of 1 to 5 molar equivalents relative to the mixture of a compound represented by Formula (XIIa) and a compound represented by Formula (XIIb), preferably in the range of 1.5 to 3 molar equivalents, and more preferably in the range of 2 to 2.5 molar equivalents.

A solvent used in the reaction is not particularly limited as long as it is stable under relevant reaction conditions and does not inhibit the target reaction. Since the yield of a compound represented by Formula (II), which is a product, depends on the type of solvent, it is preferable to use an ether-based solvent such as THF.

With regard to the amount of reaction solvent used, it may be used at 1 to 100 times by mass relative to the mixture of a compound represented by Formula (XIIa) and a compound represented by Formula (XIIb), is preferably in the range of 3 to 20 times by mass, and is more preferably in the range of 5 to 10 times by mass.

The reaction temperature may usually be −80° C. to 0° C., and is preferably −60° C. to −40° C., The reaction time is usually 0.5 hours to 6 hours, and is preferably 1 to 3 hours.

Furthermore, the hydroxy group of the mixture of a compound represented by Formula (XIIa) and a compound represented by Formula (XIIb) may be protected by a tert-butyldimethylsilyl group and the like and then subjected to a cyclopropanation reaction. By building a cyclopropane ring and then removing the protecting group, a compound represented by Formula (II) is obtained.

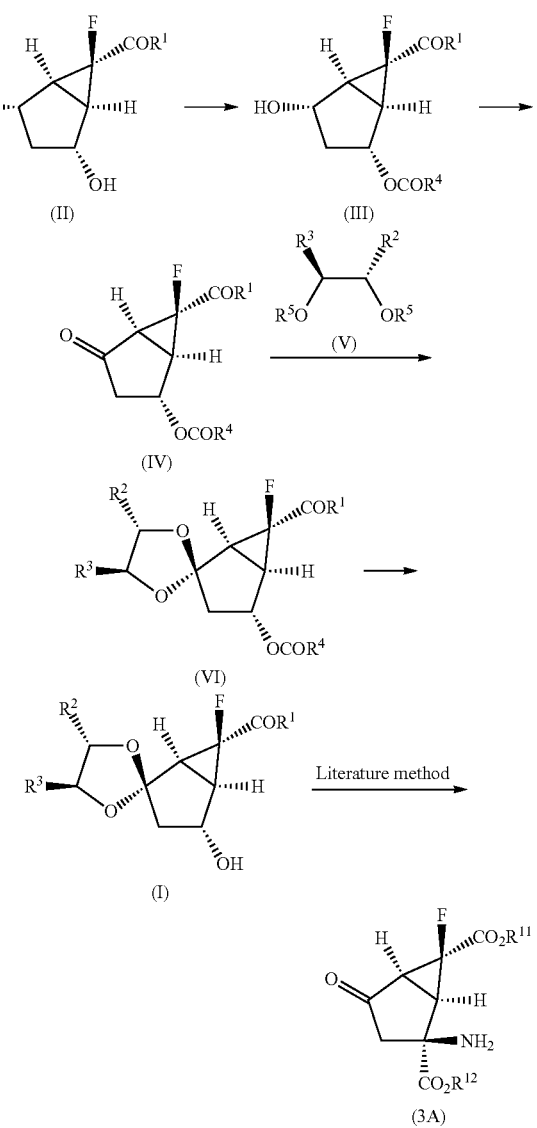

Scheme 2

(Scheme 2)

In the formulae, $R^1$, $R^2$, $R^3$, $R^4$, $R^5$, $R^{11}$, and $R^{12}$ are as defined above.

By protecting only one of the two hydroxy groups of a compound represented by Formula (II), a compound represented by Formula (III) is obtained.

The present reaction gives a desired stereoisomer in the presence of an appropriate enzyme.

In a preferred embodiment of the present reaction, by reacting a compound represented by Formula (II) with an acyl group donor in the presence of an enzyme, a compound represented by Formula (III) is obtained.

As the enzyme, a microorganism-produced enzyme having stereoselective acylation capability is used. By reacting a compound represented by Formula (II) and an acyl group donor in an organic solvent and the like in the presence of this enzyme, stereoselective acylation can be carried out. Furthermore, by immobilizing the enzyme on a support, it may also be used in the reaction as an immobilized enzyme. In this case, after a compound represented by Formula (II) is mixed with an acyl group donor in an organic solvent and the like, a support having an enzyme immobilized thereon is added to the above mixture and stirred, or a column is charged with a support having an enzyme immobilized thereon, and the above mixture is passed through the column, thus carrying out a stereoselective acylation reaction. The reaction temperature may usually be −20° C. to 60° C. The organic solvent and the like used are not particularly limited as long as it is stable under relevant reaction conditions and does not inhibit the target reaction. Since the yield and optical purity of a compound represented by Formula (III), which is a product, depend on the type of solvent, it is preferable to use an organic solvent such as toluene, isopropyl ether, tetrahydrofuran, n-hexane, n-heptane, acetone, or chloroform or an ionic liquid such as 1-butyl-3-methylimidazolium hexafluorophosphate or 1-butyl-3-methylimidazolium tetrafluoroborate (Org. Lett., 2, 4189 (2000)).

Examples of the acyl group donor include vinyl acetate, isopropenyl acetate, vinyl propionate, isopropenyl propionate, vinyl butanoate, isopropenyl butyrate, vinyl caproate, isopropenyl caproate, vinyl caprate, isopropenyl caprate, vinyl caprylate, isopropenyl caprylate, vinyl chloroacetate, isopropenyl chloroacetate, vinyl pivalate, and isopropenyl pivalate, and it is preferably vinyl acetate.

The microorganism as an enzyme source is preferably a fungus or a bacterium. It is more preferably at least one type of fungus or bacterium selected from the group consisting of the *Candida* genus, the *Aspergillus* genus, the *Thermomyces* genus, the *Penicillium* genus, the *Humicola* genus, the *Geotrichum* genus, the *Galactomyces* genus, and the *Burkholderia* genus, and it is yet more preferably at least one type of fungus or bacterium selected from the group consisting of *Candida antaretica, Aspergillus niger, Aspergillus melleus, Thermomyces langinosus, Penicillium camemberti, Humicola* sp., *Geotrichum candidum, Geotrichum eriense, Geotrichum fermentans, Galactomyces geotrichum,* and *Burkholderia cepacia.*

The microorganism-derived enzyme is preferably a lipase or an acylase, and more preferably *Candida antarctica*-derived lipase A. The microorganism-derived enzyme may be purified from an extract in which a microorganism is ground or a culture supernatant in accordance with a standard method. It is not always necessary to purify the microorganism-derived enzyme as a single product, and it may also be used as a crude enzyme. The enzyme may be used on its own or a plurality of types thereof may be used as a mixture. It is also possible to obtain a commercial product.

Examples of commercial *Candida antarctica*-derived lipase A products include NOVOZYM CALAL (trade name, available from Novozymes Japan Ltd.), NOVOZYM 735 (trade name, available from Novozymes Japan Ltd.), CHIRAZYME L-5 lye (trade name, available from Roche Diagnostics K.K.), and Lipase A CLEA (trade name, available from Sigma-Aldrich Japan).

Examples of commercial *Candida antaretica*-derived lipase B products include NOVOZYM 435 (trade name, available from Novozymes Japan Ltd.).

Examples of the other lipases include Lipase AS "Amano" (trade name, available from Amano Enzyme Inc. [*Aspergillus niger*-derived lipase]), Lipozym TL 100L IM (trade name, available from Novozymes Japan Ltd. [*Thermomyces langinosus*-derived immobilized lipase]), Lipozym TL 100 (trade name, available from Novozymes Japan Ltd. [*Thermomyces langinosus*-derived lipase]), CHIRAZYME L8 Lyo (trade name, available from Roche Diagnostics K.K. [*Humicola* sp.-derived lipase]), Lipase G "Amano" (trade name, available from Amano Enzyme Inc. [*Penicillium camemberti*-derived lipase]), and Lipase PS "Amano" SD (trade name, available from Amano Enzyme Inc. [*Burkholderia cepacia*-derived lipase]).

Examples of acylases include Acylase 15000 "Amano" (trade name, available from Amano Enzyme Inc, [*Aspergillus melleus*-derived acylase]).

The microorganism-derived enzyme may also be immobilized on a support and used as an immobilized enzyme. Examples of the support used for immobilization of the enzyme include Celite or a Toyonite (Toyonite 200, Toyonite 200P, Toyonite 200M, Toyonite 200A (available from Toyo Denka Kogyo Co., Ltd.)). Other than an immobilized enzyme obtained by immobilizing the above-mentioned commercial lipase, an enzyme immobilized by applying a cultured cell supernatant obtained by culturing a specific microorganism to the above support may be used as an enzyme having lipase activity. As the specific microorganism, *Geotrichum candidum, Geotrichum eriense, Geotrichum fermentans, Galactomyces geotrichum,* and the like are preferable.

Subsequently, by oxidizing the hydroxy group of a compound represented by Formula (III), a compound represented by Formula (IV) is obtained.

In a preferred embodiment of the present reaction, by reacting a compound represented by Formula (III) with an oxidizing agent in the presence of a catalyst, a compound represented by Formula (IV) is obtained.

Examples of the catalyst include $RuCl_3$ and 2,2,6,6-tetramethylpiperidine 1-oxyl (TEMPO).

The amount of catalyst used is not particularly limited as long as it is an amount that does not inhibit the reaction and does not cause a side reaction, but it may usually be used in the range of 0.001 to 1 molar equivalents relative to the compound represented by Formula (III), and preferably in the range of 0.01 to 0.1 molar equivalents.

Examples of the oxidizing agent include sodium hypochlorite.

The amount of oxidizing agent used is not particularly limited as long as it is an amount that does not inhibit the reaction and does not cause a side reaction, but it may usually be used in the range of 1 to 3 molar equivalents relative to the compound represented by Formula (III), and preferably in the range of 1 to 1.5 molar equivalents.

A solvent used in the reaction is not particularly limited as long as it is stable under relevant reaction conditions and does not inhibit the target reaction. Since the yield of a compound represented by Formula (IV), which is a product, depends on the type of solvent, it is preferably dichloromethane, chloroform, chlorobenzene, acetonitrile, and the like, and more preferably dichloromethane.

With regard to the above solvent, one type may be used on its own or two or more types may be used as a mixture.

The amount of reaction solvent used may be 1 to 100 times by mass relative to the compound represented by Formula (III), and is preferably in the range of 3 to 10 times by mass.

The reaction temperature may usually be −20° C. to 50° C., preferably −20° C. to 20° C., and more preferably −10° C. to 0° C.

The reaction time is usually 0.5 hours to 6 hours, and preferably 1 to 3 hours.

Furthermore, the oxidation reaction of the hydroxy group of a compound represented by Formula (III) may be carried out by a method (for example, Swern oxidation and the like) well known to a person skilled in the art, and a compound represented by Formula (IV) is obtained.

Subsequently, by reacting a compound represented by Formula (IV) with a compound represented by Formula (V) in the presence of an acid catalyst, a compound represented by Formula (VI) is obtained.

Examples of the acid catalyst include trifluoromethanesulfonic acid and trimethylsilyl trifluoromethanesulfonate.

The amount of acid catalyst used is not particularly limited as long as it is an amount that does not inhibit the reaction and does not cause a side reaction, but it may usually be used in the range of 0.01 to 1 molar equivalents relative to the compound represented by Formula (IV), preferably in the range of 0.05 to 0.5 molar equivalents, and more preferably in the range of 0.1 to 0.3 molar equivalents.

A solvent used in the reaction is not particularly limited as long as it is stable under relevant reaction conditions and does not inhibit the target reaction. Since the yield of a compound represented by Formula (VI), which is a product, depends on the type of solvent, it is preferable to use dichloromethane, toluene, and the like.

With regard to the above solvents, one type may be used on its own or two or more types may be used as a mixture.

Furthermore, depending on the circumstances, it may also be used as a dehydrated solvent by the use of an appropriate dehydrating agent or desiccant.

The amount of reaction solvent used may be 1 to 100 times by mass relative to a compound represented by Formula (IV), and is preferably in the range of 5 to 20 times by mass.

The reaction temperature may usually be $-20°$ C. to $50°$ C., preferably $-10°$ C. to $30°$ C., and more preferably $-10°$ C. to $0°$ C.

Examples of compounds represented by Formula (V) include (1S,2S)-1,2-diphenylethane-1,2-diol, (4S,5S)-2,2,7,7-tetramethyl-4,5-diphenyl-3,5-dioxa-2,7-disil aoctane, (2S,3S)-butane-2,3-diol, and (4S,5S)-2,2,4,5,7,7-hexamethyl-3,6-dioxa-2,7-disilaoctane.

The amount of compound represented by Formula (V) used is not particularly limited as long as it is an amount that does not inhibit the reaction and does not cause a side reaction, but it may usually be in the range of 1 to 3 molar equivalents relative to the compound represented by Formula (IV), and preferably in the range of 1 to 2 molar equivalents.

Subsequently, by removing the protecting group of the hydroxy group of the compound represented by Formula (VI) in the presence of a base, a compound represented by Formula (I) is obtained.

Examples of the base include an alkali metal carbonate such as sodium hydrogen carbonate, sodium carbonate, potassium hydrogen carbonate, or potassium carbonate, an alkali metal alkoxide such as sodium methoxide, sodium ethoxide, or potassium tert-butoxide, an alkali metal hydride such as sodium hydride or potassium hydride, an alkali metal hydroxide such as sodium hydroxide or potassium hydroxide, and an organic amine such as triethylamine or 1,8-diazabicyclo[5.4.0]-7-undecene; it is preferably an alkali metal carbonate such as sodium hydrogen carbonate, sodium carbonate, potassium hydrogen carbonate, or potassium carbonate, and more preferably sodium hydrogen carbonate.

The amount of base used is not particularly limited as long as it is an amount that does not inhibit the reaction and does not cause a side reaction, but it may usually be used in the range of 0.1 to 3 molar equivalents relative to the compound represented by Formula (VI), and preferably in the range of 0.5 to 1.5 molar equivalents.

A solvent used in the reaction is not particularly limited as long as it is stable under relevant reaction conditions and does not inhibit the target reaction. Since the yield of a compound represented by Formula (VI), which is a product, depends on the type of solvent, it is preferably an alcohol such as methanol, ethanol, or 2-propanol, and more preferably methanol.

With regard to the above solvents, one type may be used on its own or two or more types may be used as a mixture.

The amount of reaction solvent used may be used at 1 to 100 times by mass relative to the compound represented by Formula (IV), and is preferably in the range of 5 to 20 times by mass.

The reaction temperature may usually be $0°$ C. to $100°$ C.; it is preferably $30°$ C. to $60°$ C., and more preferably $40°$ C. to $50°$ C.

The reaction time is usually 0.5 hours to 10 hours, and preferably 1 hour to 3 hours.

A bicyclo[3.1.0]hexane derivative mGluR modulator represented by Formula (IA) and a salt thereof may be produced from a compound of Formula (I) by a method known in the art. For example, WO05/47215 and Yasuda et al., J. Org. Chem., 70, 8027 (2005) describe methods for synthesizing a compound represented by Formula (IA) using a compound represented by Formula (I).

Another embodiment of the production method of the present invention is shown in Scheme 3 below.

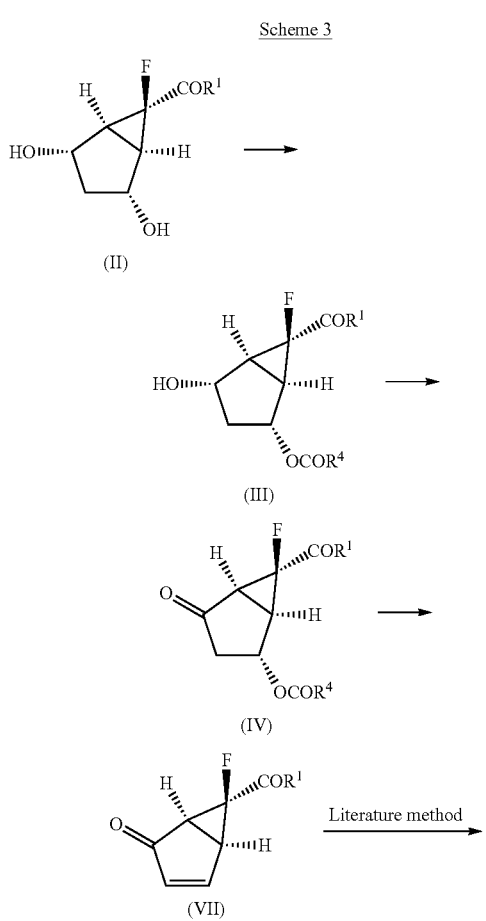

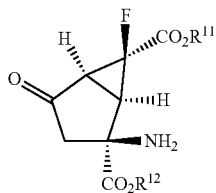

In the formulae, $R^1$, $R^4$, $R^{11}$, and $R^{12}$ are as defined above. A method for producing a compound represented by Formula (IV) from a compound represented by Formula (II) is as described above.

By making a base or an acid act on a compound represented by Formula (IV), a compound represented by Formula (VII) is obtained.

Examples of the base include an organic amine such as triethylamine or 1,8-diazabicyclo[5.4.0]-7-undecene.

The amount of base used is not particularly limited as long as it is an amount that does not inhibit the reaction and does not cause a side reaction, but it may usually be used in the range of 0.5 to 3 molar equivalents relative to the compound represented by Formula (IV), and preferably in the range of 0.8 to 1.2 molar equivalents.

Examples of the acid include trifluoromethanesulfonic acid and silica gel.

The amount of acid used is not particularly limited as long as it is an amount that does not inhibit the reaction and does not cause a side reaction, but it may usually be used in the range of 0.1 to 3 molar equivalents relative to the compound represented by Formula (IV)

A solvent used in the reaction is not particularly limited as long as it is stable under relevant reaction conditions and does not inhibit the target reaction. It is preferable to use dichloromethane or methanol.

A bicyclo[3.1.0]hexane derivative mGluR modulator represented by Formula (IA) and a salt thereof may be produced from the compound of Formula (VII) above by a method known in the art. For example, Nakazato et al., J. Med. Chem., 43, 4893-4909 (2000) describes a method for synthesizing a compound represented by Formula (IA) using a compound represented by Formula (VII).

Another embodiment of the production method of the present invention is shown in Scheme 4 below.

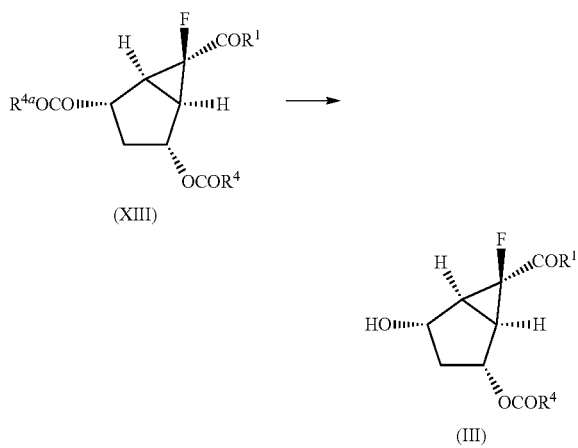

In the formulae, $R^1$, $R^4$, and $R^{4a}$ are as defined above.

The present reaction gives a desired stereoisomer in the presence of an appropriate enzyme.

In a preferred embodiment of the present reaction, by reacting a compound represented by Formula (XIII) as an acyl group donor with an acyl group acceptor in the presence of an enzyme, only one of the two acyl groups of the compound represented by Formula (XIII) is selectively cleaved, and a compound represented by Formula (III) is obtained.

As the enzyme, a microorganism-produced enzyme having stereoselective ester exchange reactivity is used. Furthermore, by immobilizing the enzyme on a support, it may also be used in the reaction as an immobilized enzyme. In this case, after a compound represented by Formula (XIII) is mixed with an acyl group acceptor in an organic solvent and the like, a support having an enzyme immobilized thereon is added to the above liquid mixture and stirred, or a column is charged with a support having an enzyme immobilized thereon and the above liquid mixture is passed through the column, thus carrying out a stereoselective ester exchange reaction. The reaction temperature is usually −20° C. to 60° C. The organic solvent and the like used in the reaction are not particularly limited as long as they are stable under relevant reaction conditions and do not inhibit the target reaction. From the viewpoint of the yield and optical purity of the compound represented by Formula (III), it is preferable to use an organic solvent such as toluene, isopropyl ether, tetrahydrofuran, n-hexane, n-heptane, acetone, or chloroform or an ionic liquid such as 1-butyl-3-methylimidazolium hexafluorophosphate or 1-butyl-3-methylimidazolium tetrafluoroborate (Org. Lett., 2, 4189 (2000)). It is yet more preferable to use isopropyl ether.

Examples of the acyl group acceptor include methanol, ethanol, n-propanol, benzyl alcohol, cyclopentanol, 2-propanol (isopropanol), and 2-butanol, and it is preferably cyclopentanol, 2-propanol (isopropanol), or 2-butanol. The most desirable compound for the enzymatic reaction is cyclopentanol.

The microorganism as an enzyme source is preferably a fungus or a bacterium. It is more preferably at least one type of fungus or bacterium selected from the group consisting of the *Candida* genus, the *Aspergillus* genus, the *Alcaligenes* genus, the *Pseudomonas* genus, the *Dipodascus* genus, the *Penicillium* genus, and the *Burkholderia* genus, and yet more preferably at least one type of fungus or bacterium selected from the group consisting of *Candida rugosa, Aspergillus niger, Pseudomonas stutzeri, Pseudomonas fluorescens, Pseudomonas* sp., *Penicillium roqueforti, Dipodascus australiensis, Alcaligenes* sp., and *Burkholderia cepacia*.

The microorganism-derived enzyme is preferably a lipase or an esterase, and more preferably an *Alcaligenes* sp.-, *Burkholderia cepacia*-, *Pseudomonas fluorescens*-, or *Candida rugosa*-derived lipase. The microorganism-derived enzyme may be purified from an extract in which a microorganism is ground or a culture supernatant in accordance with a standard method. It is not always necessary to purify the microorganism-derived enzyme as a single product, and a crude enzyme may also be used The enzyme may be used on its own or a plurality of types may be used as a mixture. It is also possible to obtain a commercial product.

Examples of *Alcaligenes* sp.-derived lipase products include Lipase QLM (trade name, available from Meito Sangyo Co., Ltd.) Examples of *Burkholderia* cepacia-derived lipase products include Lipase PS "Amano" SD (trade name, available from Amano Enzyme Inc.). Examples of *Pseudomonas fluorescens*-derived lipase products include Lipase AK "Amano" 20 (trade name, available from Amano Enzyme Inc.). Examples of *Candida rugosa*-derived lipase products include Lipase AY "Amano" 30G (trade name, available from Amano Enzyme Inc.)

Examples of other lipases include Lipase R "Amano" (trade name, available from Amano Enzyme Inc. [*Penicillium roqueforti*-derived lipase]), Lipase TL (trade name, available from Meito Sangyo Co., Ltd. [*Pseudomonas stutzeri*-derived lipase]), and Lipase AS "Amano" (trade name, available from Amano Enzyme Tno. [*Aspergillus niger*-derived lipase]).

Examples of esterases include CHE "Amano" 2 (sample name, available from Amano Enzyme Inc. [*Pseudomonas* sp.-derived esterase]).

The microorganism-derived enzyme may also be immobilized on a support and used as an immobilized enzyme. Examples of the support used for immobilization of the enzyme include Celite and a Toyonite (Toyonite 200, Toyonite 200P, Toyonite 200M, Toyonite 200A (available from Toyo Denka Kogyo Co., Ltd.)). Other than an immobilized enzyme obtained by immobilizing the above-mentioned commercial lipases, an enzyme immobilized by applying to the above support a cultured cell supernatant obtained by culturing a *Dipodascus australiensis* NBRC 10805 microorganism strain may also be used as an enzyme having ester exchange capability.

Here, the starting materials and reagents may be either commercial products, ones known from the literature, or ones prepared in accordance with a method described in literature related to analogous compounds. Reaction and purification of a product obtained as a result of the reaction are in accordance with methods known to a person skilled in the art. Examples of purification methods include crystallization, distillation, and normal phase or reversed phase chromatography.

EXAMPLES

More specific examples are illustrated below, but the disclosure of the present invention is not limited thereto. Examples 1 to 4, 18, and 19 show the method of Scheme 1. Examples 5 to 9 and 12 to 17 show the method of Scheme 2. Examples 10 and 11 show the method of Scheme 3.

Example 1

Mixture of dimethyl fluoro[(1R,5R)-5-hydroxycyclopent-2-en-1-yl]propanedioate (10a) and dimethyl fluoro[(1S,5S)-5-hydroxycyclopent-2-en-1-yl]propanedioate (10b)

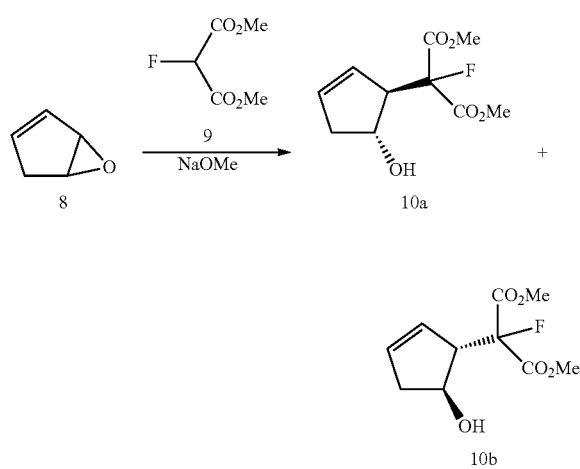

23.01 g (110.2 mmol) of a 25 w/w % methanol solution of sodium methoxide was added to a methanol (90.4 mL) solution of 18.19 g (121.2 mmol) of dimethyl fluoropropanedioate (9) over 3 minutes while keeping the internal temperature between 25° C. and 30° C. After stirring the solution thus obtained for 15 minutes, 4.52 g (55.1 mmol) of 6-oxabicyclo[3.1.0]hex-2-ene (8) was added thereto over 2 minutes while keeping the internal temperature between 25° C. and 38° C. After stirring at room temperature for 1 hour, 45 mL of a saturated ammonium chloride aqueous solution was added over 10 minutes while keeping the internal temperature between 26° C. and 35° C. The reaction mixture was concentrated under reduced pressure, most of the methanol was removed by evaporation, and 108 g of a brown solution containing solids was obtained. After extraction with 136 mL of ethyl acetate was carried out twice, washing with 45 mL of water was carried out. After the organic layer was concentrated under reduced pressure, 100 mL of toluene was added, and concentration under reduced pressure was carried out again. The concentrated residue was purified by flash silica gel column chromatography (eluent: toluene/ethyl acetate), thus giving 7.21 g of a mixture of the compound of Formula 10a and the compound of Formula lab as a yellow oily material.

$^1$H NMR (500 MHz, DMSO-d$_6$): δ 2.13-2.17 (m, 1H), 2.56 (dddd, J=2.2, 4.3, 7.1, 17.2 Hz, 1H), 3.32-3.40 (m, 1H), 3.77 (s, 3H), 3.79 (s, 3H), 4.20 (m, 1H), 5.04 (d, J=6.1 Hz, 1H), 5.47 (ddd, J=2.1, 4.3, 6.1 Hz, 1H), 5.85 (ddd, J=2.2, 4.4, 6.1 Hz, 1H).

$^{13}$C NMR (125 MHz, DMSO-d$_6$) δ 41.93, 53.39 (d, J=19.5 Hz), 58.70 (d, J=20.8 Hz), 70.43 (d, J=2.6 Hz), 93.55, 95.14, 125-59, 133.32, 165.42 (d, J=15.6 Hz), 165.62 (d, J=14.3 Hz).

$^{19}$F NMR (470 MHz, DMSO-d$_6$); δ −172.43, −172.36. HRMS (ES) m/z:

[M+Na]$^+$ calcd for C$_{10}$H$_{13}$O$_5$FNa; 255.0645, found 255.0635. IR (neat) 3528, 3408, 2960, 1755, 1438, 1284, 1253, 1173, 1111, 1060, 1031, 936, 838, 787, 722, 668, 415 cm$^{-1}$,

Example 2-1

Mixture of methyl fluoro[(1R,5R)-5-hydroxycyclopent-2-en-1-yl]acetate (11a) and methyl fluoro[(1S,5S)-5-hydroxycyclopent-2-en-1-yl]acetate (11b)

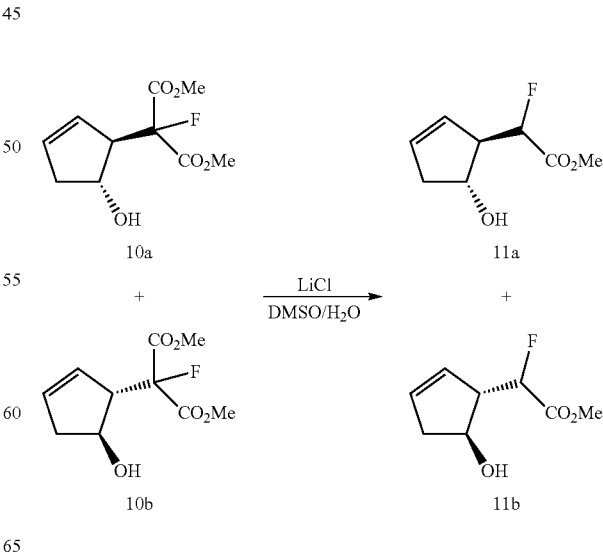

172.51 g of dimethyl sulfoxide and 25.92 g of water were added to 17.27 g (74.50 mmol) of a mixture of the compound of Formula 10a and the compound of Formula 10b. 9.65 g (227.65 mmol) of lithium chloride was added to this solution, and the mixture was heated and stirred at 130° C. for 2 hours. After allowing it to cool, the reaction mixture was extracted with 500 mL of ethyl acetate three times, and the organic layer was then concentrated under reduced pressure, thus giving a concentrated residue. This concentrated residue was purified by flash column silica gel chromatography (eluent: n-hexane/ethyl acetate=1:1), thus giving 3.674 g of a mixture of the compound of Formula 11a and the compound of Formula 11b as a yellow oily material.

$^1$H NMR (500 MHz, DMSO-$d_6$): δ 2.11-2.17 (m, 1.6H), 2.53-2.60 (m, 1.6H), 2.87-2.96 (m, 1.6H), 3.71 (s, 1.8H), 3.73 (s, 3H), 4.23-4.28 (m, 1.6H), 4.93 (d, J=5.0 Hz, 0.6H), 5.07 (d, J=5.4 Hz, 1H), 5.11 (dd, J=4.2, 48.3 Hz, 0.6H), 5.17 (dd, J=3.8, 48.5 Hz, 1H), 5.42-5.45 (m, 1H), 5.55-5.58 (m, 0.6H), 5.78-5.80 (m, 1.6H). $^{13}$C NMR (125 MHz, DMSO-$d_6$): δ 41.29, 41.83, 51.95, 52.13, 56.80 (d, J=20.8 Hz), 57.06 (d, J=19.5 Hz), 70.49 (d, J=5.2 Hz), 71.90 (d, J=2.6 Hz), 88.36 (d, J=184.3 Hz), 88.48 (d, J=184.3 Hz), 125.93 (d, J=5.2 Hz), 127.28 (d, J=3.9 Hz), 131.76, 132.13, 169.05 (d, J=24.7 Hz), 169.21 (d, J=24.7 Hz). $^{19}$F NMR (470 MHz, DMSO-d): δ −197.87 (dd, J=29.2, 47.5 Hz), −194.53 (dd, 3-25.7, 47.8 Hz). HRMS (ES) m/z: [M+Na]$^+$ calcd for $C_8H_{11}O_3FNa$; 197.0590, found 197.0578. IR (neat) 3410, 3060, 2956, 2851, 1747, 1440, 1357, 1288, 1228, 1127, 1097, 1067, 1048, 1025, 952, 856, 724, 584, 450 cm$^{-1}$.

Example 2-2

Mixture of methyl fluoro[(1R,5R)-5-hydroxycyclopent-2-en-1-yl]acetate (11a) and methyl fluoro[(1S,5S)-5-hydroxycyclopent-2-en-1-yl]acetate (11b)

70.06 g of dimethyl sulfoxide and 45.64 g (33.16 mol) of triethylamine hydrochloride were added to 70.02 g (0.3015 mmol) of a mixture of the compound of Formula 10a and the compound of Formula 10b, and the mixture was heated and stirred at 110° C. to 120° C. for 5 hours. After allowing it to cool, 350.9 g of water was added thereto, and the reaction mixture was extracted with 350 g of methyl isobutyl ketone twice. The organic layer was concentrated under reduced pressure, thus giving 65.40 g of a yellowish brown oily material containing 46.78 g (value quantitatively determined by gas chromatograph) of a mixture of the compound of Formula 11a and the compound of Formula 11b.

Example 2-3

Mixture of methyl fluoro[(1R,5R)-5-hydroxycyclopent-2-en-1-yl]acetate (11a) and methyl fluoro[(1S,5S)-5-hydroxycyclopent-2-en-1-yl]acetate (11b)

1 mL of dimethyl sulfoxide, 0.073 g (1.25 mmol) of sodium chloride, and 0.061 g (1.00 mmol) of acetic acid were added to 0.232 g (1.00 mmol) of a mixture of the compound of Formula 10a and the compound of Formula 10b, and the mixture was heated and stirred at 110° C. to 120° C. for 5 hours. After allowing it to cool, analysis was carried out using a high-performance liquid chromatograph, and it was found that 0.146 g (value quantitatively determined by high-performance liquid chromatograph) of a mixture of the compound of Formula 11a and the compound of Formula 11b was obtained.

Example 3

Mixture of methyl fluoro[(1R,2S,3R,5S)-3-hydroxy-6-oxabicyclo[3.1.0]hex-2-yl]a cetate (12a) and methyl fluoro[(1s,2R,3S,5R)-3-hydroxy-6-oxabicyclo[3.1.0]hex-2-yl]a cetate (12b)

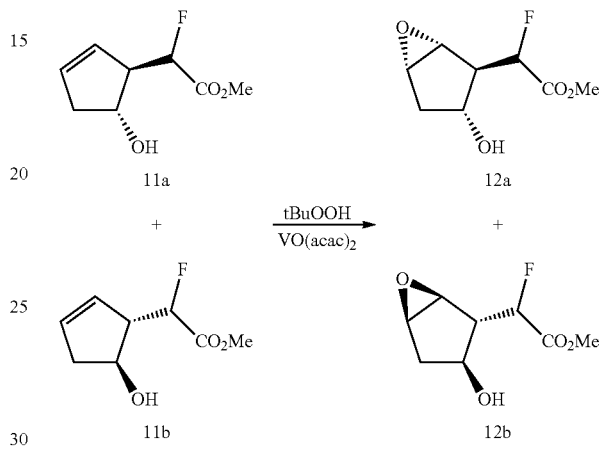

0.1176 g (0.444 mmol) of vanadyl acetylacetonate (VO(acac)$_2$) was added to a chlorobenzene (18.37 g) solution of 3.644 g (20.92 mmol) of a mixture of the Compound of Formula 11a and the compound of Formula 11b at room temperature. The mixture was heated to 60° C., and 5.445 g (42.29 mmol) of a 70% toluene solution of tert-butyl hydroperoxide (tBuOOH) was added thereto over 10 minutes while keeping the internal temperature between 55° C. and 60° C. The mixture was stirred at 55° C. for 4 hours and then allowed to cool to room temperature. After 22 g of a 20% sodium thiosulfate aqueous solution was added and stirring was carried out for 30 minutes, extraction was carried out with 50 mL of ethyl acetate four times. The organic layers were combined and concentrated under reduced pressure, thus giving a concentrated residue. This concentrated residue was purified by flash silica gel column chromatography (eluent: n-hexane/ethyl acetate=2:1 to 1:1), thus giving 2.402 g of a mixture of the compound of Formula 12a and the compound of Formula 12b as a yellow oily material.

$^1$H NMR (500 MHz, DMSO-$d_6$): δ 1.76 (s, 0.6H), 1.79 (s, 1H), 1.99 (dt, J=7.6, 1.5 Hz, 1H), 2.02 (dt, J=1.6, 1.5 Hz, 0.6H), 2.42-2.44 (m, 0.6H), 2.48-2.51 (m, 1H), 3.38 (d, J=2.5 Hz, 1H), 3.55-3.56 (m, 1.6H), 3.59 (m, 0.6H), 3.75 (s, 1.8H), 3.77 (s, 3H), 4.08 (t, J=6.9 Hz, 0.6H), 4.18 (t, J=6.9 Hz, 1H), 4.41 (d, J=6.5 Hz, 0.6H), 4.49 (d, J=6.1 Hz, 1H), 5.32 (dd, J=4.0, 47.0 Hz, 1H), 5.35 (dd, J=3.0, 98.0 Hz, 0.6H). NMR (125 MHz, DMSO-$d_6$): δ 37.37, 37.88, 51.87 (d, 3=19.5 Hz), 51.93 (d, J=18.2 Hz), 52.34, 52.42, 56.83 (d, J=7.8 Hz), 57.73, 57.84, 58.20 (d, J=2.6 Hz), 70.85 (d, 3=5.2 Hz), 72.65 (d, J=2.6 Hz), 125.93 (d, J=181.7 Hz), 127.28 (d, J=183.0 Hz), 168.63 (d, J=23.9 Hz), 168.71 (d, J=24.7 Hz). $^{19}$F NMR (470 MHz, DMSO-$d_6$): δ −198.56 (dd, J=32.9, 47.5 Hz), −198.20 (dd, J=32.9, 48.0 Hz). HRMS (ES) m/z: [M+Na]$^+$ calcd for $C_8H_{11}O_4FNa$; 213.0539, found 213.0530. IR (neat)

3506, 3032, 2959, 1758, 1639, 1440, 1408, 1364, 1288, 1226, 1098, 1077, 1012, 965, 917, 838, 802, 732, 668, 564, 444 cm$^{-1}$.

Example 4

Methyl (1R,2R,4S,5S,6R)-6-fluoro-2,4-dihydroxybicyclo[3.1.0]hexane-6-carboxylate (2)

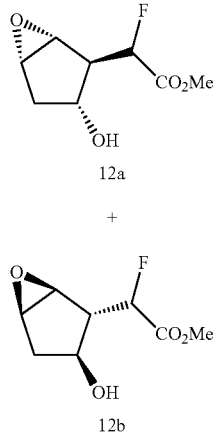

A THF (dehydrated, 20 mL) solution of 2.334 g (12.27 mmol) of a mixture of the compound of Formula 12a and the compound of Formula 12b was cooled to −50° C., and 29.0 mL (27.26 mmol) of a 0.94 mol/L triethylaluminum hexane solution was added thereto over 30 minutes while keeping the internal temperature between −60° C. and −50° C. After stirring at −50° C. for 30 minutes, 23.6 mL (23.60 mmol) of a 1 mol/L lithium hexamethyldisilazide (LiHMDS) hexane solution was added thereto over 45 minutes while keeping the internal temperature between −50° C. and −40° C. After stirring at −50° C. for 2 hours, the reaction mixture was added over 30 minutes to 44.3 g of a 25% citric acid aqueous solution cooled to 5° C. This reaction mixture was extracted with 50 mL of ethyl acetate four times and concentrated under reduced pressure. The concentrated residua was purified by flash silica gel column chromatography (eluent: ethyl acetate), thus giving a yellow oily material. This oily material was precipitated from a mixed liquid of 3.0 g of ethyl acetate and 0.5 g of water, thus giving 1.027 g of the compound of Formula 2 as colorless crystals.

mp 73.9-76.5° C., $^1$H NMR (500 MHz, DMSO-d$_6$): δ 1.64 (dd, 3=4.4, 15.3 Hz, 1H), 1.96 (m, 1H), 2.17 (s, 2H), 3.72 (br s, 3H), 4.18 (d, J=5.0 Hz, 2H), 4.93 (br s, 2H). $^{13}$C NMR (125 MHz, DMSO-d$_6$): δ 38.03 (d, 3-11.7 Hz), 45.76 (d, =7.8 Hz), 52.64, 71.53, 77.52, 79.42, 168.78 (d, J=26.0 Hz). $^{19}$F NMR (470 MHz, DMSO-d$_6$): δ −216.927. HRMS (ES) m/z: [M+Na]$^+$ calcd for C$_8$H$_{11}$O$_4$FNa; 213.0539, found 213.0537. IR (KBr) 3549, 3413, 3295, 3246, 2964, 2922, 1732, 1616, 1467, 1442, 1381, 1336, 1285, 1265, 1235, 1198, 1181, 1130, 1078, 1041, 994, 947, 890, 805, 777, 733, 646, 566, 537, 480 cm$^{-1}$.

Example 5

Methyl (1R,2R,4S,5S,6R)-2-(acetyloxy)-6-fluoro-4-hydroxybicyclo[3.1.0]hexane-6-carboxylate (3)

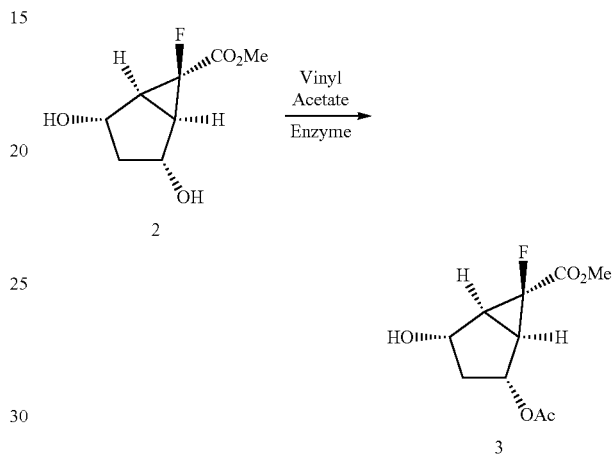

A 50 mL Sumilon tube (Sumitomo Bakelite Co., Ltd.) was charged with 12.0 mL of NOVOZYM 735, 6.0 g of Toyonite 200M, and 30 mL of a 100 mM potassium phosphate buffer (pH 7) and shaken (100 rpm) at room temperature (25° C.) for 18 hours. After shaking was completed, the mixture was filtered using Kiriyama filter paper No. 5B and then dried under reduced pressure at room temperature for 4 days, thus giving an immobilized enzyme. A 6 mL volume column (Bond Elut Reservoir with frit: purchased from GL Sciences Inc.) was charged with 2.0 g of the immobilized enzyme thus obtained.

A solution in which 3.1 g of crystals of the compound of Formula 2 was dissolved in 136.5 mL of vinyl acetate/acetone (10:1) was fed to the column charged with the above immobilized enzyme via a silicone tube using a peristaltic pump (Atto Corporation). The feed rate was 20 mL/hr.

After feeding was completed, the eluate was analyzed by a TLC method and an HPLC method, and it was found that 2.95 g (yield 79.05%) of the compound of Formula 3 was obtained at an optical purity of 99.99% e.e. The eluate was concentrated under reduced pressure and the concentrated residue was then purified by flash silica gel column chromatography (eluent: n-hexane/ethyl acetate), thus giving the compound of Formula 3 as a colorless oily material.

$^1$H NMR (500 MHz, CDCl$_3$): δ 1.96 (dd, J=4.6, 16.1 Hz, 1H), 2.11 (s, 3H), 2.28 (ddd, J=6.1, 13.4, 16.4 Hz, 1H), 2.37 (br s, 1H), 2.41 (d, J=6.9 Hz, 1H), 2.44 (d, J=6.5 Hz, 1H), 3.82 (s, 3H), 4.45 (d, J=5.7 Hz, 1H), 5.29 (d, J=6.1 Hz, 1H). $^{13}$C NMR (125 MHz, CDCl$_3$): δ 21.17, 34.96 (d, J=10.4 Hz), 37.93 (d, J=11.7 Hz), 42.44 (d, J=9.1 Hz), 52.91, 72.90, 75.49, 79.33, 168.55 (d, J=25.9 Hz), 170.28. $^{19}$F NMR (470 MHz, CDCl$_3$): δ −217.73. HRMS (ES) m/z: [M+Na]$^+$ calcd for C$_{10}$H$_{13}$O$_5$FNa; 255.0645, found 255.0628. IR (neat):

3451, 2960, 1739, 1442, 1373, 1318, 1232, 1115, 1074, 1045, 1016, 993, 950, 867, 800, 788, 736, 654, 629, 608, 573, 473 cm$^{-1}$.

Example 6

Methyl (1R,2R,5S,6S)-2-(acetyloxy)-6-fluoro-4-oxobicyclo[3.1.0]hexane-6-carboxylate (4)

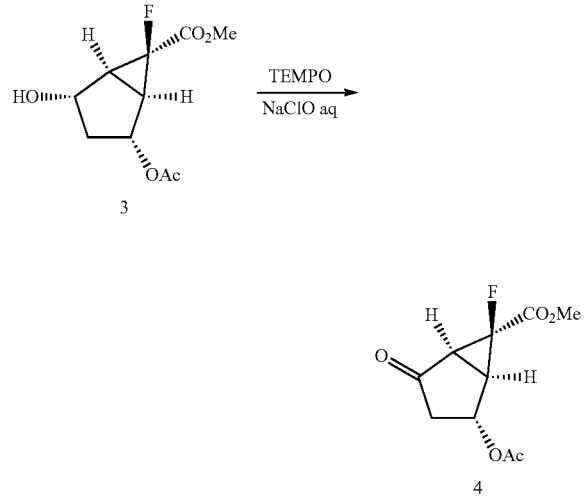

A dichloromethane (dehydrated, 5 mL) solution of 1.10 g (4.74 mmol) of the compound of Formula 3 was cooled to −10° C., 15.1 mg (0.097 mmol) of 2,2,6,6-tetramethylpiperidine 1-oxyl (TEMPO), 109.2 mg (1.30 mmol) of sodium hydrogen carbonate, and 2.2 mL of water were added in sequence, and 4,230 g (5.68 mmol) of a 10% sodium hypochlorite aqueous solution was then added while keeping the internal temperature between −10° C. and 0° C. After stirring at −10° C. to 0° C. for 1 hour, the mixture was separated. The aqueous layer was re-extracted with 10 mL of toluene, and the dichloromethane layer and the toluene layer were each washed with 1 mL of water. After the organic layers were combined and concentrated under reduced pressure, 10 mL of toluene was added, and the mixture was again concentrated under reduced pressure, thus giving 972 mg of a pale yellow oily material. By precipitating from toluene, 512.5 mg of the compound of Formula was obtained as colorless crystals.

mp: 88.4-88.9° C., $^1$H NMR (500 MHz, CDCl$_3$): δ 2.12 (s, 3H), 2.37 (dd, J=3.8, 19.5 Hz, 1H), 2.66 (dt, J=19.5, 5.9 Hz, 1H), 2.73 (d, J=6.1 Hz, 1H), 2.93 (dd, J=1.5, 6.1 Hz, 1H), 3.86 (8, 3H), 5.50 (d, J=6.1 Hz, 1H). $^{13}$C NMR (125 MHz, CDCl$_3$): δ 20.86, 38.18 (d, J=10.4 Hz), 38.99 (d, J=14.3 Hz), 43.48 (d, J=3.9 Hz), 53.41, 69.09 (d, J=2.5 Hz), 79.26, 166.42 (d, J=25.9 Hz), 170.02, 204.35. $^{19}$F NMR (470 MHz, CDCl$_3$): δ −210.68. MS m/z 230.0 [M]$^+$. IR (KBr): 3102, 2995, 1756, 1738, 1441, 1397, 1373, 1348, 1326, 1305, 1260, 1219, 1173, 1108, 1084, 1037, 1024, 1012, 983, 954, 907, 870, 829, 782, 738, 651, 640, 626, 474, 461 cm$^{-1}$.

Example 7

Methyl (1S,4R,4'S,5R,5'S, 6S)-4-(acetyloxy)-6-fluoro-4',5'-diphenyls piro[bicyclo[3.1.0]hexane-2,2-[1,3]dioxolane]-6-carboxylate (6)

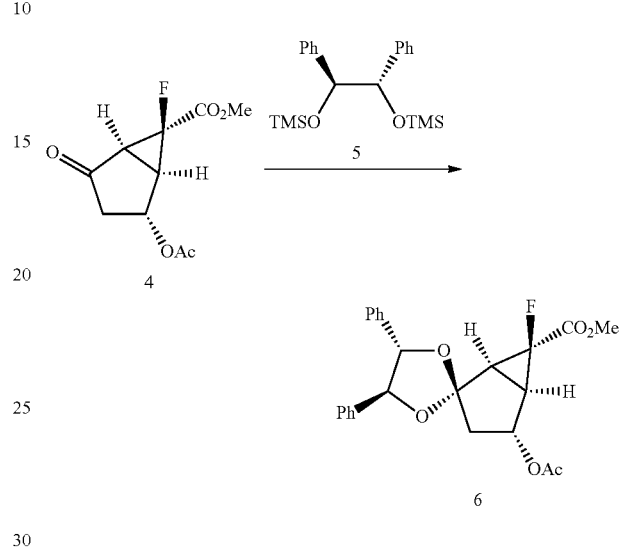

A dichloromethane (dehydrated, 19 mL) solution of 5.00 g (23.34 mmol) of (1S,2S)-1,2-diphenylethane-1,2-diol was heated to 30° C., 1.5 mg (0.006 mmol) of iodine and 4.54 g (28.13 mmol) of 1,1,1-trimethyl-N-(trimethylsilyl)silanamine (HMDS) were added thereto in sequence, and stirring was then carried out at 35° C. for 1 hour. After allowing it to cool to room temperature, the mixture was concentrated under reduced pressure. 25 mL of toluene was added to the concentrated residue, and the mixture was again concentrated under reduced pressure. After this was repeated twice, 5 mL of toluene was added thereto, thus giving 13.66 g of a toluene solution of (4S,5S)-2,2,7,7-tetramethyl-4,5-diphenyl-3,6-dioxa-2,7-disil aoctane (5) (Solution 1)

1.203 g (1.97 mmol) of Solution 1 was added to a dichloromethane (dehydrated, 3 mL) solution of 401 mg (1.74 mmol) of crystals of the compound of Formula 4, this solution was cooled to −10° C., and a dichloromethane (dehydrated, 1 mL) solution of 35.7 mg (0.161 mmol) of trimethylsilyl trifluoromethanesulfonate (TMSOTf) was added thereto. After stirring was carried out at −10° C. for 3.5 hours, 1.238 g (1.89 mmol) of Solution 1 above was added. After stirring was carried out at −10° C. for a further 3 hours, a dichloromethane (dehydrated, 1 mL) solution of 39.6 mg (0.178 mmol) of trimethylsilyl trifluoromethanesulfonate (TMSOTf) was added. After stirring was carried out at −10° C. overnight, 0.03 mL (0.371 mmol) of pyridine was added, and stirring was carried out at 0° C. for 20 minutes. 1 mL of a 5% sodium hydrogen carbonate aqueous solution was added, and the mixture was stirred at 0° C. for 20 minutes and then separated. The aqueous layer was re-extracted with 2 mL, of dichloromethane twice, and the organic layers were combined and washed with 1 mL of water. After concentrating under reduced pressure, the concentrated residue was purified by flash silica gel column chromatography (eluent: n-hemane/ethyl acetate), and precipitation was then carried out from methanol, thus giving 326.4 mg of the compound of Formula 6 as colorless crystals.

mp: 123.5-123.7° C., $^1$H NMF (500 MHz, CDCl$_3$): δ 2.11 (s, 3H), 2.46 (dd, J=4.3, 15.2 Hz, 1H), 2.47 (d, J=6.9 Hz, 1H), 2.56 (d, J=6.9 Hz, 1H), 2.60 (dt, J=15.9, 6.3 Hz, 1H), 3.86 (s, 3H), 4.79 (d, J=8.2 Hz, 1H), 4.88 (d, J=8.2 Hz, 1H), 5.38 (d, 6.3 Hz, 1H), 7.19-7.21 (m, 2H), 7.26-7.31 (m, 5H), 7.33-7.35 (m, 3H). $^{13}$C NMR (125 MHz, CDCl$_3$): δ 21.20, 34.85 (d, J=11.3 Hz), 37.26 (d, J=12.6 Hz), 43.95 (d, J=7.4 Hz), 53.05, 72.91, 78.80, 85.67, 86.19, 117.52, 126.22, 126.83, 128.32, 128.47, 128.54, 128.60, 136.08, 136.82, 168.51 (d, J=24.9 Hz), 170.56. $^{19}$F NMR (470 MHz, CDCl$_3$): δ −216.72. MS m/z: 449.1 [M+Na]$^+$. IR (KBr): 3456, 3068, 2964, 2916, 1737, 1606, 1497, 1456, 1442, 1359, 1330, 1258, 1238, 1197, 1133, 1102, 1053, 1024, 986, 936, 916, 870, 822, 791, 765, 755, 700, 683, 648, 608, 531, 466 cm$^{-1}$.

Example 8

Methyl (1S,4R,4'S,5R,5'S,6S)-4-(acetyloxy)-6-fluoro-4',5'-diphenylspiro[bicyclo[3.1.0]hexane-2,2-[1,3]dioxolane]-6-carboxylate (6)

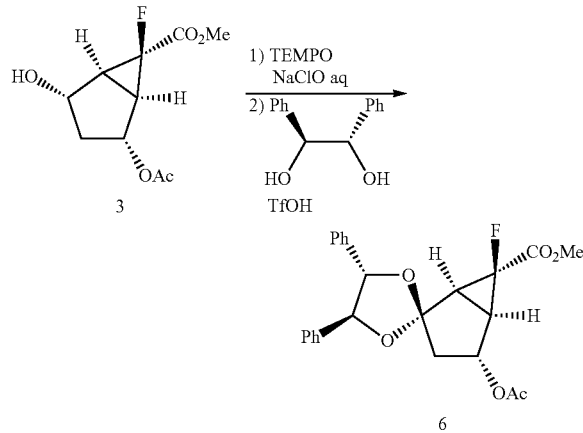

A dichloromethane (dehydrated, 5 mL) solution of 1.003 g (4.32 mmol) of the compound of Formula 3 was cooled to −10° C., 14.5 mg (0.093 mmol) of 2,2,6,6-tetramethylpiperidine 1-oxyl (TEMPO), 99.2 mg (1.18 mmol) of sodium hydrogen carbonate, and 2 mL of water were added in sequence, and 3.854 g (5.18 mmol) of a 10% sodium hypochlorite aqueous solution was then added while keeping the internal temperature between −10° C. to 0° C. The mixture was stirred at −10° C. to 0° C. for 1 hour and then separated. The organic layer was washed with 1 mL of water, then dried with sodium sulfate, and concentrated under reduced pressure, and 1.05 g of the compound of Formula 4 was obtained as a yellow oily material. 1.111 g (5.19 mmol) of (1S,2S)-1,2-diphenylethane-1,2-diol was added to a dichloromethane (18 mL) solution of the compound of Formula 4 thus obtained, this solution was cooled to −5° C., and a dichloromethane (dehydrated, 2 mL) solution of 131.8 mg (0.88 mmol) of trifluoromethanesulfonic acid was then added. After stirring at −5° C. for 2 hours and at room temperature for 20 hours, 0.1 mL (1.24 mmol) of pyridine was added, and stirring was carried out at 0° C. for 20 minutes. 1.6 mL of a 5% sodium hydrogen carbonate aqueous solution was added thereto, and the mixture was stirred at 0° C. for 20 minutes and then separated. The aqueous layer was extracted with 5 mL of dichloromethane twice, and the organic layers were combined and washed with 2 mL of water. The organic layer was dried with sodium sulfate and then concentrated under reduced pressure, and the concentrated residue was purified by flash silica gel column chromatography (eluent; n-hexane/ethyl acetate), thus giving 1.388 g of the compound of Formula 6 in amorphous form. By precipitating from methanol, 947 mg of colorless crystals were obtained.

$^1$H NMR (300 MHz, CDCl$_3$) δ 2.12 (s, 3H) 2.43-2.49 (m, 2H), 2.56-2.65 (m, 2H), 3.87 (s, 3H), 4.80 (d, J=8.2 Hz, 1H), 4.89 (d, J=8.2 Hz, 1H), 5.39 (d, J=6.1 Hz, 1H), 7.18-7.39 (m, 10H).

MS m/z: 449.2 [M+Na]$^+$.

Example 9

Methyl (1S,4R,4'S,5R,5'S,6S)-6-fluoro-4-hydroxy-4',5'-diphenylspiro[bicyclo[3.1.0]hexane-2,2-[1,3]dioxolane]-6-carboxylate (1)

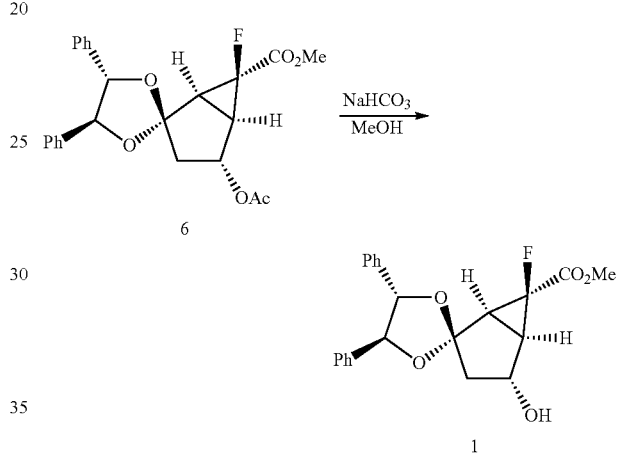

Methanol (dehydrated, 2 mL) was added to 201.3 mg (0.472 mmol) of crystals of the compound of Formula 6, and the mixture was heated to 50° C. to thus dissolve the crystals. 40.4 mg (0.481 mmol) of sodium hydrogen carbonate was added to this solution, after stirring was carried out at 45° C. to 50° C. for 1.5 hours 19.9 mg (0.237 mmol) of sodium hydrogen carbonate was further added, and stirring was carried out for a further 2 hours. The reaction mixture was concentrated under reduced pressure, most of the methanol was removed by evaporation, 4 mL of toluene was added to a solid thus obtained and the mixture was heated to 50° C., 1 mL of water was added, and the mixture was stirred and separated. The aqueous layer was re-extracted with 4 mL of toluene, and the organic layers were combined and concentrated under reduced pressure, thus giving 194.7 mg of a white solid. By precipitation from a heptane/ethyl acetate (3/2) mixed solvent, 101.3 mg of the compound of Formula 1 was obtained as colorless crystals.

mp: 120.3-120.7° C., $^1$H NMR (500 MHz, CDCl$_3$): δ 2.35 (dd, J=4.0, 15.5 Hz, 1H), 2.38 (d, J=6.9 Hz, 1H), 2.48 (d, J=6.9 Hz, 1H), 2.51 (dt, J=15.3, 5.7 Hz, 1H), 2.61 (d, J=9.6 Hz, 1H), 3.86 (s, 3H), 4.48 (dd, J=5.4, 9.6 Hz, 1H), 4.80 (d, J=8.4 Hz, 1H), 4.82 (d, J=8.4 Hz, 1H), 7.18 (dd, J=3.1, 6.5 Hz, 2H), 7.26 (dd, J=2.9, 67 Hz, 2H), 7.29-7.31 (m, 3H), 7.34-7.36 (m, 3H). $^{13}$C NMR (125 MHz, CDCl$_3$): δ 36.76 (d, J=13.0 Hz), 37.56 (d, J=11.7 Hz), 45.89 (d, J=7.8 Hz), 52.99, 70.90, 79.67, 85.96, 86.09, 117.71, 126.29, 126.85, 128.35, 128.44, 128.59, 128.68, 135.79, 136.45, 168.82 (d, J=25.9 Hz). $^{19}$F NMR (470 MHz, CDCl$_3$): δ −216.52. MS m/z: 407.2

[M+Na]+. IR (KBr): 3568, 3065, 3030, 2957, 2888, 1737, 1607, 1497, 1446, 1379, 1324, 1306, 1230, 1145, 1111, 1055, 1026, 1012, 987, 913, 868, 824, 760, 699, 678, 647, 600, 540, 478 cm$^{-1}$.

Example 10

Methyl (1S,5S,6S)-6-fluoro-4-oxobicyclo[3.1.0]hex-2-ene-6-carboxyla to (7)

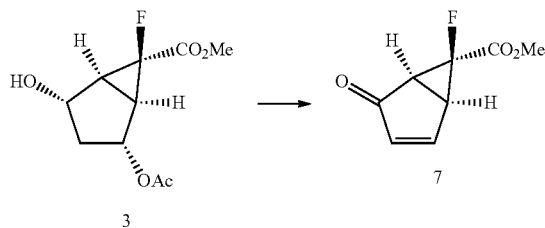 [SMILES: COC(=O)[C@]1(F)[C@@H]2[C@H]1[C@@H](O)C[C@H]2OC(C)=O ; COC(=O)[C@@]1(F)[C@@H]2C(=O)C=C[C@@H]21]

An acetonitrile (0.5 mL) solution of 106.2 mg (0.457 mmol) of the compound of Formula 3 was cooled to −5° C., 1.9 mg (0.012 mmol) of 2,2,6,6-tetramethylpiperidine 1-oxyl (TEMPO), 11.5 mg (0.137 mmol) of sodium hydrogen carbonate, and 0.2 mL of water were added in sequence, and 0.4 mL (0.537 mmol) of a 10% sodium hypochlorite aqueous solution was then added while keeping the internal temperature between −10° C. and 0° C. After stirring at −10° C. to 0° C. for 4 hours, 0.1 mL of a 10% sodium thiosulfate aqueous solution was added, and the mixture was stirred and separated. The aqueous layer was re-extracted with 5 mL of toluene three times, and the organic layers were combined and concentrated under reduced pressure. The concentrated residue was purified by flash silica gel column chromatography (eluent: n-hexane/ethyl acetate), thus giving 38.6 mg of the compound of Formula 7 as a colorless oily material.

$^1$H NMR (300 MHz, CDCl$_3$): δ 2.79 (m, 1H), 3.23 (dd, J=3.0, 5.7 Hz, 1H), 3.86 (s, 3H), 6.07 (dd, J=0.6, 5.6 Hz, 1H), 7.42 (m, 1H). MS m/z 170.0 [M]+.

Example 11

Methyl (1S,5S,6S)-6-fluoro-4-oxobicyclo[3.1.0]hex-2-ene-6-carboxyla to (7)

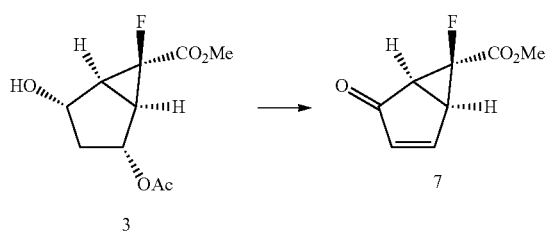 [SMILES: COC(=O)[C@]1(F)[C@@H]2[C@H]1[C@@H](O)C[C@H]2OC(C)=O ; COC(=O)[C@@]1(F)[C@@H]2C(=O)C=C[C@@H]21]

A dichloromethane (dehydrated, 5 mL) solution of 983 mg (4.23 mmol) of crystals of the compound of Formula 3 was cooled to −10° C., 13.7 mg (0.089 mmol) of 2,2,6,6-tetramethylpiperidine 1-oxyl (TEMPO), 101.6 mg (1.21 mmol) of sodium hydrogen carbonate, and 2 mL of water were added in sequence, and 3.844 g (5.16 mmol) of a 10% sodium hypochlorite aqueous solution was then added while keeping the internal temperature between −10° C. and 0° C. After stirring at −10° C. to 0° C. for 1 hour, the mixture was separated. The organic layer was washed with 1 mL of water, then dried with sodium sulfate and concentrated under reduced pressure, and 1.0824 g of the compound of Formula 4 was obtained as a yellow oily material. 0.63 mL (4.07 mmol) of 1,8-diazabicyclo[5.4.0]-7-undecene was added to a dichloromethane (18 mL) solution of the compound of Formula 4 thus obtained, stirring was carried out at room temperature for 1 hour, 4.2 mL of 1N hydrochloric acid was then added, and the mixture was stirred and separated. After the aqueous layer was re-extracted with 5 mL of dichloromethane, the organic layer was washed with 5 mL of saturated brine. The organic layer was dried with sodium sulfate and then concentrated under reduced pressure, and the concentrated residue was purified by flash silica gel column chromatography (eluent: n-hexane/ethyl acetate), thus giving 567 mg of the compound of Formula 7 as a colorless oily material.

$^1$H NMR (500 MHz, CDCl$_3$): δ 2.78-2.79 (m, 1H), 3.24 (dd, J=3.0, 6.0 Hz, 1H), 3.85 (s, 3H), 6.06 (d, J=5.5 Hz, 1H), 7.43 (dd, J=2.8, 5.8 Hz, 1H). $^{13}$C NMR (125 MHz, CDCl$_3$): δ 34.00 (d$_r$ J=14.3 Hz), 34.42 (d, J=13.0 Hz), 53.15, 89.77 (d, J=259.2 Hz), 133.26, 152.34 (d, J=2.6 Hz), 166.03 (d, J=26.0 Hz), 198.54. $^{19}$F NMR (470 MHz, CDCl$_3$): δ −214.93. MS m/z: 169.0 [M−H]$^-$

Examples 12 to 19 below show the results of examining reaction conditions in order to obtain the compound of Formula 3 by asymmetrically acetylating the compound of Formula 2 using various microorganism-derived enzymes.

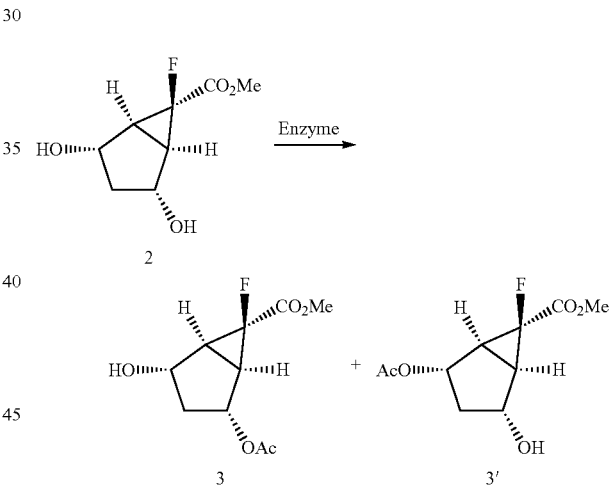

The state of the starting material compound of Formula 2 and formation of the target compound of Formula 3 and its enantiomer, the compound of Formula 3', were confirmed by the TLC method and the HPLC method below.

(TLC method: TLC plate; silica gel Si60 (Art 1.5715, Merck & Co., Inc.))
Developing solvent; n-hexane/ethyl acetate=10/1
Coloration; anisaldehyde/conc. sulfuric acid/acetic acid=1/2/100
Rf value; compound of Formula 2=0.20, compounds of Formula 3 and Formula 3'=0.40
(HPLC method: column CHIRALCEL OJ-RH 4.6 mm ID×150 mm L (Daicel Chemical Industries, Ltd.))
Mobile phase; methanol/0.1% phosphoric acid aqueous solution=38/62
Flow rate; 0.8 mL/min
Temperature; 35° C.
Detection; UV 195 nm Retention time;
compound of Formula 2: 3.8 min
compound of Formula 3; 10.3 min
compound of Formula 3': 9.0 min Example 12

Enzyme Screening 50 mg of an enzyme to be tested was placed in a 10 mL stoppered test tube, 2.7 mL of vinyl acetate, 0.3 mL of acetone, and 20 mg of the compound of Formula 2 were added thereto, and stirring was carried out using a stirrer at 25° C. for 18 to 98 hours (600 rpm). After the reaction was completed, enzyme residue was removed by filtration using an Ekicrodisc 25CR (Pall Corporation, diameter 25 mm), the solution was dried under reduced pressure and then dissolved in 1 mL of methanol, and part thereof was then sampled and subjected to TLC analysis and HPLC analysis. The 41 types of enzymes shown in Table 1, Table 2, and Table 3 were screened.

From the results of TLC analysis, in reactions using the enzymes shown in Table 1 and Table 2, spots that had an Rf value on TLC coinciding with the Rf value (0.40) of an authentic racemic sample (compound of Formula 3 and compound of Formula 3') and exhibited the same color (brown) were detected. Among enzymes for which the detection of an acetylated form was prominent in the TLC analysis, those for which the target product compound of Formula 3 was confirmed by HPLC analysis are shown in Table 1 with the amount of target product formed and the optical purity. Furthermore, among enzymes for which the detection of an acetylated form was prominent in the TLC analysis, those for which the optical isomer compound of Formula 3', which is different from the target product, was confirmed by HPLC analysis are shown in Table 2 with the amount thereof formed and the optical purity.

In the present Examples, enzymes for which formation of neither the compound of Formula 3 nor the compound of Formula 3' was detected are shown in Table 3.

TABLE 1

| Enzyme name (trade name) | Derived from | Amount of 3 formed (mg) | % e.e. of 3 |
|---|---|---|---|
| Lipase A CLEA | Candida antarctica Lipase A | 17.82 | 94.06 |
| Novozym 735 | Candida antarctica Lipase A | 14.25 | 96.34 |
| Lipozym TL 100L IM | Thermomyces langinosus | 2.93 | 39.87 |
| Novozym 435 | Candida antarctica Lipase B | 0.17 | 99.99 |

TABLE 2

| Enzyme name (trade name) | Derived from | Amount of 3' formed (mg) | % e.e. of 3' |
|---|---|---|---|
| Lipase C. cylindracea | Candida cylindracea | 13.57 | 66.04 |
| Lipase AYS "Amano" | Candida rugosa | 4.54 | 36.99 |
| Lipase AK "Amano" 20 | Pseudomonas fluorescens | 3.15 | 34.41 |
| Lipase AY "Amano" 30G | Candida rugosa | 1.84 | 48.06 |
| Sumizyme CT-L | Thermomyces langinosus | 1.64 | 99.99 |
| Lipase R | Penicillium roqueforti | 0.67 | 99.99 |

TABLE 2-continued

| Enzyme name (trade name) | Derived from | Amount of 3' formed (mg) | % e.e. of 3' |
|---|---|---|---|
| Lipase AS "Amano" | Aspergillus niger | 0.57 | 57.18 |
| Lipase A "Amano" 6 | Aspergillus niger | 0.52 | 49.00 |
| Lipase PS "Amano" SD | Burkholderia cepacia | 0.51 | 25.50 |
| CHE "Amano" 2 | Pseudomonas sp. | 0.43 | 48.02 |
| Sumizyme NSL3000 | Aspergillus niger | 0.39 | 99.99 |
| Pectinase G "Amano" | Aspergillus pulverulentus | 0.32 | 99.99 |
| Nuclease "Amano" G | Penicillium citrinum | 0.13 | 99.99 |

TABLE 3

| Enzyme name (trade name) | Derived from |
|---|---|
| Acylase 15000 | Aspergillus melleus |
| Protease P "Amano" | Aspergillus melleus |
| Lipase M "Amano" 10 | Mucor javanicus |
| Deamizyme | Aspergillus melleus |
| Lipase II | Porcine Pancreas |
| Lipozyme IM20 | Rhizomucor miehei |
| Lactase F | Aspergillus oryzae |
| Lipase F-AP-15 | Rhizopus oryzae |
| Papain W-40 | Carica papaya |
| Lipase G | Penicillium camemberti |
| Protease M "Amano" | Aspergillus oryzae |
| Protease N "Amano" G | Bacillus subtilis |
| Newlase F3G | Rhizopus niveus |
| Protease S "Amano" G | Bacillus stearothermophilus |
| Sumizyme PLE | Aspergillus niger |
| Catalase Nagase | Micrococcus lysodeikticus |
| Amylase AD "Amano" | Bacillus subtilis |
| Sumizyme PGO | Penicillium chrysogenum |
| Novozym CALBL | Candida antarctica |
| Bromelain F | Ananas comosus M |
| Proleather FG | Bacillus sp. |
| Sumityme MMR | Rhizomucor miehei |
| Lipozym TL 100 | Thermomyces langinosus |
| Subtilicin A | Bacillus subtilis |

Example 13

Enzyme Immobilization Examination 1

Examination of immobilization of NOVOZYM 735 (product name, Novozymes Japan Ltd.; *Candida antarctica* Lipase A-derived) by Toyonite (Toyonite)

50 mL volume Sumilon tubes (Sumitomo Bakelite Co., Ltd.) were charged with 1 g of Toyonite 200, Toyonite 200P, Toyonite 200M, and Toyonite 200A, to these were added 18 mL of a 100 mM potassium phosphate buffer (pH 7) and 2 mL of NOVOZYME 735, and shaking at 120 rpm was carried out at 10° C. for 15 hours. After shaking was completed, filtering was carried out using a Kiriyama funnel (No. 6 filter paper used), washing/filtering was carried out with 10 mL of a 100 mM potassium phosphate buffer (pH 7), air drying was carried out for 10 minutes, and further drying was carried out in a vacuum desiccator at room temperature for 4 hours, thus giving four types of immobilized enzymes, that is, NOVOZYM 735/Toyonite 200, NOVOZYM 735/Toyonite 200P, NOVOZYM 735/Toyonite 200M, and NOVOZYM 735/Toyonite 200A.

For each of the four types of immobilized enzymes 10 mg was placed in a 10 mL stoppered test tube, to this were added 1 mL of vinyl acetate, 0.2 mL of acetone, and 50 mg of crystals of 2, and a reaction was carried out by stirring (570 rpm) using a stirrer at 37° C. for 20 hours. After the reaction was completed, the immobilized enzyme was removed by filtration using an Ekicrodisc 25CR. (Pall Corporation, diameter 25 mm), and the solution was dried under reduced pressure, dissolved in 1 mL of methanol, and then subjected to HPLC analysis. The amount of the target product compound of Formula 3 formed and its optical purity are shown in Table 4.

TABLE 4

| Enzyme name (trade name)/support | Amount of 3 formed (wg) | % e.e. of 3 |
| --- | --- | --- |
| NOVOZYM 735/Toyonite 200 | 26.96 | 99.99 |
| NOVOZYM 735/Toyonite 200P | 46.49 | 89.52 |
| NOVOZYM 735/Toyonite 200M | 35.04 | 99.99 |
| NOVOZYM 735/Toyonite 200A | 28.38 | 99.99 |

Example 14

Enzyme Immobilization Examination 2

1 to 10 g of 10 types of enzymes (Lipase AS "Amano", Acylase 1500 "Amano", Lipase PS Amano SD, Lipase G "Amano" 50, Lipase AYS "Amano", Lipase R "Amano", Lipase AY "Amano" 30G, Lipase AK "Amano" 20 (obtained from Amano Enzyme Inc.), pig pancreas-derived lipase type II (obtained from Sigma-Aldrich Japan), and Chirazyme L8 lyo (obtained from Roche Diagnostics K.K.)) were suspended in 30 mL of a 100 mM potassium phosphate buffer (pH 7) and filtered using Kiriyama filter paper No. 5B, the filtrates were mixed with 1 g of Toyonite 200M in 50 mL volume Sumilon tubes, and shaking at 120 rpm was carried out at room temperature (25° C.) for 17 hours 40 minutes. After shaking, they were filtered using Kiriyama filter paper No. 5B and further dried under reduced pressure at room temperature for 5 days, thus giving the respective immobilized enzymes.

For each of the 10 types of immobilized enzymes 20 mg was placed in a 10 mL stoppered test tube, to this were added 1.0 mL of vinyl acetate, 0.1 mL of acetone, and 20 mg of crystals of the compound of Formula 2, and a reaction was carried out by stirring using a stirrer (600 rpm) at 23° C. for 21 hours. After the reaction was completed, the immobilized enzyme was removed by filtration using an Ekicrodisc 25CR (Pall Corporation, diameter 25 mm), and the solution was dried under reduced pressure, dissolved in 1 mL of methanol, and then subjected to HPLC analysis. For those in which the target product compound of Formula 3 was confirmed, the amount formed and the optical purity of the target product are shown in Table 5. For those in which the compound of Formula 3', which is a different enantiomer from the target product, was confirmed, the amount formed and the optical purity thereof are shown in Table 6. Lipase PS Amano SD was an enzyme that formed the compound of Formula 3' in Example 12, but in the present enzymatic reaction, in which the enzyme was immobilized, formation of the compound of Formula 3 was detected. For pig pancreas-derived lipase type II, even when the enzyme was immobilized, no acetylation reaction was confirmed.

It is found in Table 5 that, among enzymes for which an acetylation reaction could not be detected in Example 12 and enzymes which formed the compound of Formula 3', which is a different enantiomer, there are enzymes that prominently form the target product compound of Formula 3 by immobilizing the enzyme.

TABLE 5

| Enzyme name (trade name) | Derived from | Amount of 3 formed (mg) | % e.e. of 3 |
| --- | --- | --- | --- |
| Lipase G "Amano" 50 | Penicillium camemberti | 5.86 | 86.95 |
| Acylase 1500 "Amano" | Aspergillus melleus | 2.44 | 59.76 |
| Lipase AS "Amano" | Aspergillus niger | 5.01 | 55.15 |
| Chirazyme L8 lyo | Humicola sp. | 4.18 | 27.33 |
| Lipase PS "Amano" 3D | Burkholderia cepacia. | 6.74 | 18.66 |

TABLE 6

| Enzyme name (trade name) | Derived from | Amount of 3' formed (mg) | % e.e. of 3' |
| --- | --- | --- | --- |
| Lipase AK "Amano" 20 | Pseudomonas fluorescens | 3.15 | 34.41 |
| Lipase AYS "Amano" | Candida rugosa | 4.54 | 36.99 |
| Lipase AY "Amano" 30G | Candida rugosa | 1.84 | 48.06 |
| Lipase R "Amano" | Penicillium roqueforti | 0.67 | 99.99 |

Example 15

Enzyme Immobilization Examination 3

2 mL of a liquid enzyme (LIPOZYME TL100, NOVOZYM CALBL, NOVOZYM 735 (obtained from Novozymes Japan Ltd.)) or 1 g of a powdered enzyme (Lipase AS "Amano" (obtained from Amano Enzyme Inc.)) was mixed with or dissolved in 10 mL of a 100 mM potassium phosphate buffer (pH 7) in a Sumilon tube, 1 g of Toyonite 200M or Toyonite 200P was added thereto, and shaking at 120 rpm was carried out at 10° C. for 22 hours. After shaking, the mixtures were filtered using Kiriyama filter paper No. 5B and then dried under reduced pressure at room temperature for 5 days, thus giving immobilized enzymes (8 types).

For each of the 8 types of immobilized enzymes 20 mg was placed in a 10 mL volume test tube, 1.0 mL of vinyl acetate, 0.1 mL of acetone, and 20 mg of crystals of the compound of Formula 2 were added, and a reaction was carried out by stirring using a stirrer (600 rpm) at 23° C. for 21 hours. After the reaction was completed, the immobilized enzyme was removed by filtration using an Ekicrodisc 25CR (Pall Corporation, diameter 25 mm), and the solution was dried under reduced pressure, dissolved in 1 mL of methanol, and then subjected to HPLC analysis. For those in which the target product compound of Formula 3 was confirmed, the amount formed and the optical purity of the target product are shown in Table 7. In enzymatic reactions by immobilized enzymes other than the combinations shown in Table 7, no compound of Formula 3 and no compound of Formula 3' were detected.

In enzymatic reactions by the NOVOZYM 735 immobilized enzyme, the compound of Formula 3 was detected in both cases.

TABLE 7

| Enzyme name (trade name) | Derived from | Support for immobilization | Amount of 3 formed (mg) | % e.e. of 3 |
| --- | --- | --- | --- | --- |
| Novozym 735 | Candida antarctica Lipase A | Toyonite 200P | 13.4 | 97.3 |

TABLE 7-continued

| Enzyme name (trade name) | Derived from | Support for immobilization | Amount of 3 formed (mg) | % e.e. of 3 |
|---|---|---|---|---|
| Novozym 735 | *Candida antarctica* Lipase A | Toyonite 200M | 4.3 | 99.99 |
| Lipase AS "Amano" | *Aspergillus niger* | Toyonite 200M | 3.24 | 71.09 |
| Lipozym TL 100L IM | *Thermomyces langinosus* | Toyonite 200M | 3.1 | 34.12 |

Example 16

12.5 mg of Chirazyme L-5 lyo (obtained from Roche Diagnostics K.K.), which is a freeze-dried *Candida antarctica* Lipase A enzyme, 1.2 mL of a vinyl acetate/acetone (9:1) mixture, and 54.55 mg of crystals of the compound of Formula 2 were placed in a 10 mL capped sample tube, and a reaction was carried out by stirring at 570 rpm using a stirrer at 37° C. for 22 hours. After the reaction was completed, the solids content was removed by filtration using an Ekicrodisc 25CR (Pall Corporation, diameter 25 mm), and the solution was dried under reduced pressure, dissolved in 1 mL of methanol, and then subjected to HPLC analysis. From the results, it was found that 47.78 mg of the compound of Formula 3 with an optical purity of 99.99% e.e. was obtained.

Example 17

Examination Using Immobilized Enzyme Packed in Column

A 50 mL Sumilon tube (Sumitomo Bakelite Co., Ltd.) was charged with 12.0 mL of NOVOZYM 735, 6.0 g of Toyonite 200M, and 30 mL of a 100 mM potassium phosphate buffer (pH 7), and shaking (100 rpm) was carried out at room temperature (25° C.) for 18 hours. After shaking was completed, the mixture was filtered using Kiriyama filter paper No. 5B and dried under reduced pressure at room temperature for 4 days, thus giving an immobilized enzyme. A 6 mL volume column (Bond Elut Reservoir with frit: purchased from GL Sciences Inc.) was charged with 4.0 g of the immobilized enzyme thus obtained.

A solution in which 10.09 g of crystals of the compound of Formula 2 was dissolved in 443 mL of vinyl acetate/acetone (10:1) was fed to the column charged with the above immobilized enzyme via a silicone tube using a peristaltic pump (Atto Corporation). The feed rate was 119 mL/hr. After feeding was completed, the eluate was analyzed by the TLC method and the HPLC method, and it was found that 10.71 g of the compound of Formula 3 (yield 88.34%) was obtained at an optical purity 97.58% e.e.

After the feeding above was completed, the immobilized enzyme-packed column was regenerated by drying under reduced pressure, and then stored at room temperature. A solution in which 8.89 g of crystals of the compound 2 was dissolved in 356.5 mL of vinyl acetate/acetone (10:1) was fed to the column charged with the above stored immobilized enzyme via a silicone tube using a peristaltic pump (Atto Corporation). The feed rate was 101 mL/hr.

After feeding was completed, the eluate was analyzed by the TLC method and the HPLC method, and it was found that 9.61 g of the compound of Formula 3 (yield 89-90%) was obtained at an optical purity of 98.54% e.e. The above results suggest that an immobilized enzyme obtained by immobilizing *Candida antarctica*-derived Lipase A on Toyonite 200M can be used repeatedly after regeneration.

Example 18

Preparation and Screening of Immobilized Enzyme: Analysis of Conversion Performance 111 strains of filamentous fungus or yeast (strains derived from a total of 11 genera, that is, *Mucor, Rhizopus, Candida, Dipodascus, Galactomyces, Geotrichum, Kluyveromyces, Endomyces, Zygosaccharomyces, Pichia,* and *Sporobolomyces*) were subjected to aeration agitation culture in a 200 mL Erlenmeyer flask containing 40 mL of a medium formed from defatted rice bran 3%, corn steep liquor 31, soybean oil 1%, and ammonium sulfate 0.2% (pH 6) at 18'C to 28° C. for 3 days. After culturing was completed, each microorganism culture fluid was individually transferred to a centrifuge tube, and the culture fluid was centrifuged into cells and cell supernatant by a centrifuge (8000 rpm, 12 to 15 minutes). 0.1 volume (to a volume of each microorganism cell supernatant) of a 1 M potassium phosphate pH 7 buffer and 0.5 g of Toyonite 200M support were added to each microorganism cell supernatant thus obtained (in a centrifuge tube such as a Sumilon tube) and shaken at 25° C. overnight (maximum 20 hours). After shaking was completed, the mixture was allowed to stand for 5 minutes; after the Toyonite 200M support settled down on the bottom of the centrifuge tube, an upper layer solution was removed by decantation, 15 mL of a 0.1 M potassium phosphate pH 7 to pH 7.5 buffer was added, and resuspension by stirring was carried out. This was repeated a total of two times, and the suspension was filtered under reduced pressure using a Kiriyama funnel (trade name) equipped with Kiriyama filter paper No. 5B (trade name)), thus giving each of the microorganism culture fluid supernatant-derived immobilized enzymes on the filter papers. Each immobilized enzyme was filtered and dried under reduced pressure for a few minutes on the filter, placed in a vacuum desiccator (with dry silica gel), and dried overnight (maximum 20 hours). Each of the immobilized enzymes that had completed drying was used in the enzymatic reaction below.

For each of the 111 types of immobilized enzymes obtained by the above-mentioned procedure 20 mg was placed in a 3.5 mL volume screw-topped sample tube, 1.0 mL of vinyl acetate, 0.1 mL of acetone, and 20 mg of crystals of the compound of Formula 2 were added thereto, and a reaction was carried out by stirring using a stirrer (600 rpm) at 25° C. for 21 hours. After the reaction was completed, the immobilized enzyme was removed by filtration using an Ekicrodisc 25CR, and the solution was dried under reduced pressure, dissolved in 1 mL of methanol, and then subjected to analysis by the HPLC method described above.

Among the strains (111 strains) classified into the above-mentioned 11 genera, when *Geotrichum* genus and *Galactomyces* genus strain-derived enzymes were used, the target reaction proceeded remarkably. Those for which a considerable amount of the target product compound of Formula 3 was confirmed are shown in Table 8 with strain, amount of target product formed, and optical purity.

TABLE 8

| Microorganism for preparation of immobilized enzyme | Amount of 3 formed (mg) | Optical purity of 3 |
|---|---|---|
| Geotrichum eriense NBRC10584 | 8.49 mg | 70.67% e.e. |
| Geotrichum candidum NBRC5767 | 11.26 mg | 75.90% e.e. |
| Geotrichum candidum NBRC6454 | 8.32 mg | 77.39% e.e. |
| Geotrichum candidum NBRC4597 | 12.19 mg | 75.41% e.e. |
| Geotrichum candidum NBRC4599 | 13.85 mg | 76.60% e.e. |
| Geotrichum fermentans JCM2468 | 11.87 mg | 76.22% e.e. |
| Geotrichum candidum NBRC5368 | 14.42 mg | 76.98% e.e. |
| Geotrichum candidum JCM6261 | 14.55 mg | 76.55% e.e. |
| Geotrichum candidum JCM6262 | 13.87 mg | 75.91% e.e. |
| Geotrichum candidum JCM6263 | 11.19 mg | 71.83% e.e. |
| Geotrichum candidum JCM6264 | 11.73 mg | 74.27% e.e. |
| Geotrichum candidum JCM6261 | 18.12 mg | 77.98% e.e. |
| Geotrichum candidum NBRC4602 | 17.40 mg | 77.68% e.e. |
| Geotrichum candidum JCM6266 | 15.24 mg | 76.98% e.e. |
| Geotrichum candidum JCM5222 | 15.43 mg | 74.68% e.e. |
| Geotrichum candidum JCM6259 | 12.36 mg | 74.68% e.e. |
| Geotrichum candidum JCM1747 | 12.36 mg | 76.28% e.e. |
| Geotrichum candidum NBRC4601 | 14.09 mg | 76.17% e.e. |
| Geotrichum candidum NBRC5959 | 12.81 mg | 74.74% e.e. |
| Galactomyces geotrichum JCM1945 | 10.65 mg | 73.23% e.e. |

Example 19

Immobilized Enzyme Continuous Reaction Experiment

A 500 mL volume capped plastic bottle was charged with 100 mL of NOVOZYM CALAL (trade name; obtained from Novozymes Japan, Ltd.), 100 g of Toyonite 200M, and 200 mL of a 100 mM potassium phosphate buffer (pH 7), and shaking (160 rpm) was carried out at room temperature (25° C.) for 18 hours. After shaking was completed, the mixture was filtered using Kiriyama filter paper No. 5B and dried under reduced pressure at room temperature for 4 days, thus giving an immobilized enzyme, A 6 mL volume column (Bond Elut Reservoir with frit: purchased from GL Sciences Inc.) was charged with 4.0 g of the immobilized enzyme thus obtained.

Subsequently, a solution in which 81.00 g of crystals of the compound of Formula 2 was dissolved in 2,700 mL of a solution containing 20% of acetone in vinyl acetate was prepared. The solution containing 81.0 g of Formula 2 thus obtained was fed to the column charged with the above immobilized enzyme using a silicone tube and a peristaltic pump (Atto Corporation). The feed rate was a maximum of 102 mL/hr.

After feeding was completed, the eluate was analyzed by the TLC method and the HPLC method, and it was found that 86.73 g of the compound of Formula 3 (yield 89.1%) was obtained at an optical purity of 97.14% e.e. to 98.06% e.e.

That is, it could be confirmed that at least 86.73 g of the compound of Formula 3 was obtained at an optical purity of 97.14% e.e. to 98.06% e.e. from 81.00 g of the compound of Formula 2 using 4.0 g of an immobilized enzyme.

Example 20

Vinyl Hexanoate Reaction

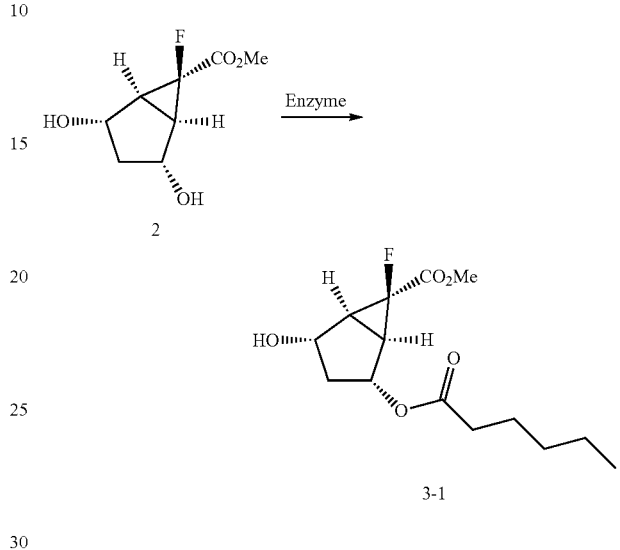

201.7 mg of the compound of Formula 2 was dissolved in a mixed solution of 7.2 mL of vinyl hexanoate and 0.8 mL of acetone, 150 mg of the same immobilized enzyme as that prepared in Example 19 was added, and an enzymatic reaction was carried out by stirring using a stirrer (600 rpm) at 25° C. for 21 hours.

After the reaction was completed, the reaction mixture was filtered using an Ekicrodisc 25CR so as to remove the immobilized enzyme and then purified by flash silica gel column chromatography (eluent: n-hexane/ethyl acetate), thus giving 15.5 mg of a compound of Formula 3-1 as a colorless solid (optical purity 76.65% e.e.)

$^1$H NMR (500 MHz, CDCl$_3$): δ 0.90 (t, J=6.5 Hz, 3H), 1.33 (m, 2H), 1.64 (m, J=7.0, 8.0 Hz, 2H), 1.94 (ddd, J=4.5, 16.0 Hz 1H), 2.28 (ddd, J=5.5, 6.0, 13.0 Hz, 1H), 2.34 (dt, J=7.5 Hz, 2H), 2.42 (5, 1H), 3.82 (s, 3H), 4.43 (dt, J=6.5 Hz, 1H), 5.31 (dt, J=6.0 Hz, 1H). $^{13}$C NMR (125 MHz, CDCl$_3$): δ 13.86, 22.26, 24.56, 31.22, 34.38, 35.04 (d, J=11.7 Hz), 37.97 (d, J=10.3 Hz), 42.53 (d, J=9.1 Hz), 52.97, 73.17, 75.33, 168.49, 168.69, 173.0. MS (Shimadzu LCMS-210EV ESI/APCI Dual positive) m/z: [M+Na]$^+$311.1

In addition, the state of the starting material compound of Formula 2 and formation of the target compound of Formula 3-1 and its enantiomer, a compound of Formula 3-1', were confirmed by the TLC method and the HPLC method below.

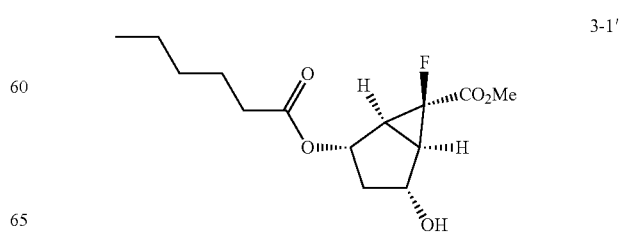

(TLC method: TLC plate; silica gel Si60 (Art 1.5715, Merck & Co., Inc.))
Developing solvent; n-hexane/ethyl acetate=10/1
Coloration; anisaldehyde/conc. sulfuric acid/acetic acid=1/2/100
Rf value; compound of Formula 2=0.20, compounds of Formula 3-1 and 3-1'=0.67
(HPLC method: column CHIRALCEL OJ-RH 4.6 mm ID×150 mm L (Daicel Chemical Industries, Ltd.))
Mobile phase; (methanol:acetonitrile=1:1)/0.1% phosphoric acid aqueous solution=52/48
Flow rate; 0.8 mL/min
Temperature; 35° C.
Detection; UV 195 nm
Retention time;
compound of Formula 3-1: 7.3 min
compound of Formula 3-1': 8.3 min Example 21

Vinyl Benzoate Reaction

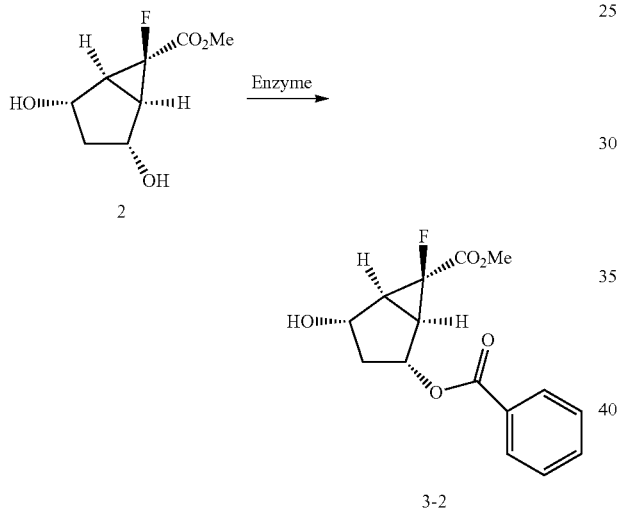

199.0 mg of the compound of Formula 2 was dissolved in a mixed solution of 7.2 mL of vinyl benzoate and 0.8 mL of acetone, 150 mg of the same immobilized enzyme as that prepared in Example 19 was added, and an enzymatic reaction was carried out by stirring using a stirrer (600 rpm) at 25° C. for 21 hours.

After the reaction was completed, the reaction mixture was filtered using an Ekicrodisc 25CR so as to remove the immobilized enzyme and then purified by flash silica gel column chromatography (eluent: n-hexane/ethyl acetate), thus giving 18.0 mg of a compound of Formula 3-2 as a colorless solid (optical purity 99.99% e.e.).

$^1$H NMR (500 MHz, CDCl$_3$): δ 2.13 (ddd, J=4.5, 16.5 Hz, 1H), 2.40 (ddd, J=3.0, 7.0, 10.0 Hz, 1H), 2.47 (dd, J=6.5 Hz, 1H), 2.59 (dd, J=6.5 Hz 1H), 3.82 (s, 3H), 4.51 (dt, J=6.0 Hz, 1H), 5.53 (dt, J=5.5 Hz 1H), 7.46 (t, J=8.0 Hz, 2H), 7.59 (t, J=8.0 Hz, 1H), 8.04 (d, J=8.5 Hz, 1H), 8.05 (d, J=8.0 Hz, 1H). $^{13}$C NMR (125 MHz, CDCl$_3$): δ 35.11 (d, J=10.3 Hz), 38.08 (d, J=11.7 Hz), 42.73 (d, J=9.1 Hz), 52.99, 73.19, 76.25, 128.49, 129.65, 133.35, 165.80, 168.46, 168.67. MS (Shimadzu LCMS-210EV ESI/APCI Dual positive) m/z: [M+Na]$^+$317.0, $[α]_D^{24}$=−11.0 deg In addition, the state of the starting material compound of Formula 2 and formation of the target compound of Formula 3-2 were confirmed by the TLC method and the HPLC method below.
(TLC method; TLC plate; silica gel Si60 (Art 1.5715, Merck & Co., Inc.))
Developing solvent; n-hexane/ethyl acetate=10/1
Coloration; anisaldehyde/conc. sulfuric acid/acetic acid=1/2/100
Rf value; compound of Formula 2=0.20, compound of Formula 3-2=0.58
(HPLC method: column CHIRALCEL OJ-RH 4.6 mm ID×150 mm L (Daicel Chemical Industries, Ltd.))
Mobile phase; (methanol:acetonitrile=1:1)/0.1% phosphoric acid aqueous solution=52/48
Flow rate; 0.8 mL/min
Temperature; 35° C.
Detection; UV 195 nm
Retention time;
compound of Formula 3-2: 8.1 min Example 22

Vinyl Pivalate Reaction

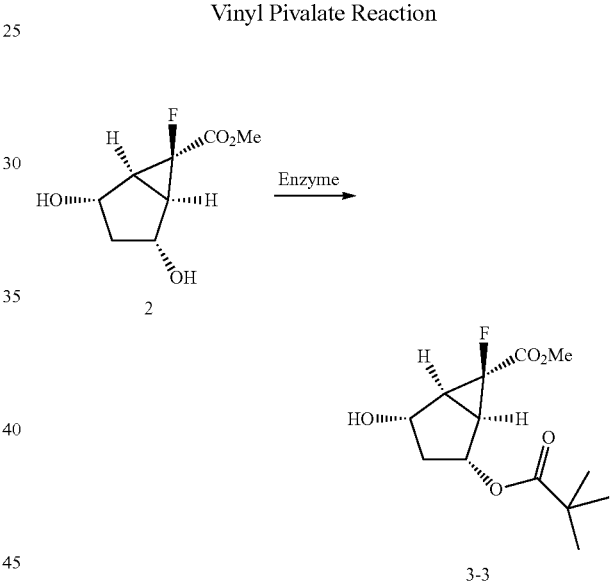

200.3 mg of the compound of Formula 2 was dissolved in a mixed solution of 7.2 mL of vinyl pivalate and 0.8 mL of acetone, 150 mg of the same immobilized enzyme as that prepared in Example 19 was added, and an enzymatic reaction was carried out by stirring using a stirrer (600 rpm) at 25° C. for 21 hours.

After the reaction was completed, the reaction mixture was filtered using an Ekicrodisc 25CR so as to remove the immobilized enzyme and then purified by flash silica gel column chromatography (eluent; n-hexane/ethyl acetate), thus giving 8.6 mg of a compound of Formula 3-3 as a colorless solid (optical purity 99.99 e.e.).

$^1$H NMR (500 MHz, CDCl$_3$): δ 1.22 (s, 9H), 1.91 (ddd, J=4.5, 16.0 Hz, 1H), 2.29 (ddd, J=5.5, 13.0 Hz, 1H), 2.41 (dd, J=6.5 Hz 1H), 2.41 (dd, J=6.0 Hz, 1H), 3.82 (s, 3H), 4.45 (dt, J=5.0, 17.5 Hz, 1H), 5.28 (dt, J=6.0 Hz 1H). $^{13}$C NMR (125 MHz, CDCl$_3$): δ 27.06, 34.90 (d, J=11.3 Hz), 31.94 (d, J=11.2 Hz), 38.65, 42.53 (d, J=8.8 Hz), 53.00, 73.22, 75.48, 168.54, 177.55, MS (Shimadzu LCMS-210EV ESI/APCI Dual positive) m/z; [M+Na]$^+$ 297.1, $[α]_D^{25}$=+6.0 deg In addition, the state of the starting material compound of Formula 2 and formation of the target compound of Formula 3-3 were confirmed by the TLC method and the HPLC method below.

(TLC method: TLC plate; silica gel 5160 (Art 1.5715, Merck & Co., Inc.))

Developing solvent; n-hexane/ethyl acetate=10/1

Coloration; anisaldehyde/conc. sulfuric acid/acetic acid=1/2/100

Rf value; compound of Formula 2=0.20, compound of Formula 3-3=0.69

(HPLC method: column CHIRALCEL OJ-RH 4.6 mm ID×150 mm L (Daicel Chemical Industries, Ltd.))

Mobile phase; (methanol:acetonitrile=1:1)/0.1% phosphoric acid aqueous solution=52/48

Flow rate; 0.8 mL/min

Temperature; 35° C.

Detection; UV 195 nm

Retention time;

compound of Formula 3-3: 5.0 min

Example 23

Vinyl Monochloroacetate Reaction

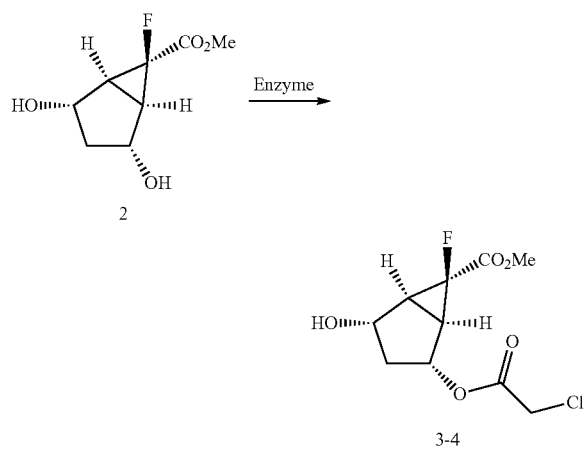

201.4 mg of the compound of Formula 2 was dissolved in a mixed solution of 7.2 mL of vinyl monochloroacetate and 0.8 mL of acetone, 150 mg of the same immobilized enzyme as that prepared in Example 19 was added, and an enzymatic reaction was carried out by stirring using a stirrer (600 rpm) at 25° C. for 21 hours.

After the reaction was completed, the reaction mixture was filtered using an Ekicrodisc 25CR so as to remove the immobilized enzyme and then purified by flash silica gel column chromatography (eluent: n-hexane/ethyl acetate), thus giving 201.2 mg of a compound of Formula 3-4 as a colorless solid (optical purity 99.99% e.e.).

$^1$H NMR (500 MHz, CDCl$_3$): δ 2.00 (ddd, J=4.5, 16.5 Hz, 1H), 2.31 (ddd, J=6.0, 13.0, 16.5 Hz, 1H), 2.43 (dd, J-=7.0 Hz, 1H), 2.47 (dd, J=7.0 Hz 1H), 3.82 (s, 3H), 4.14 (s, 2H), 4.47 (dt, J=5.5 Hz, 1H), 5.36 (dt, J=6.5 Hz 1H). $^{13}$C NMR (125 MHz, CDCl): δ 34.56 (d, J=11.2 Hz), 37.87 (d, J=11.2 Hz), 40.82, 42.27 (d, J=8.7 Hz), 52.92, 72.43, 79.07, 166.65, 168.24, 168.45. MS (Shimadzu LCMS-210EV ESI/APCI Dual positive) m/z: [M+Na]$^+$ 289.0, $[\alpha]_D^{25}$=+10.2 deg In addition, the state of the starting material compound of Formula 2 and formation of the target compound of Formula 3-4 were confirmed by the TLC method and the HPLC method below.

(TLC method: TLC plate; silica gel Si60 (Art 1.5715, Merck & Co., Inc.))

Developing solvent; n-hexane/ethyl acetate=10/1

Coloration; anisaldehyde/conc. sulfuric acid/acetic acid 1/2/100

Rf value; compound of Formula 2=0.20, compound of Formula 3-4=0.53

(HPLC method: column CHIRALCEL OJ-RH 4.6 mm ID×150 mm L (Daicel Chemical. Industries, Ltd.))

Mobile phase; (methanol:acetonitrile=1:1)/0.1% phosphoric acid aqueous solution=52/48

Flow rate; 0.8 mL/min

Temperature; 35° C.

Detection; UV 195 nm

Retention time;

compound of Formula 3-4: 4.4 min

Example 24

Vinyl Butanoate Reaction

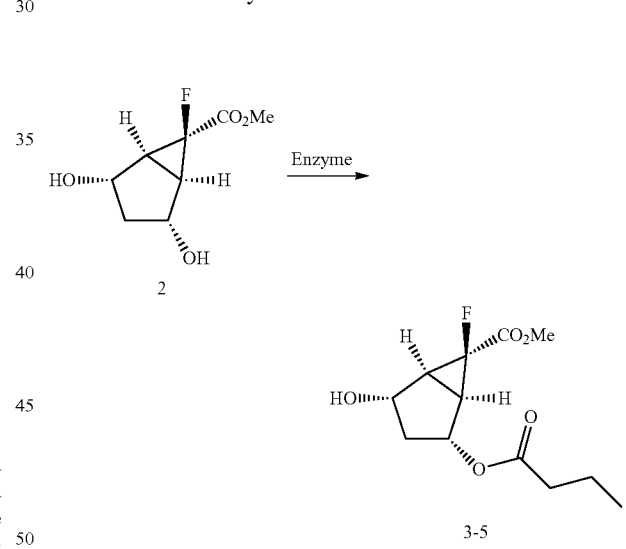

209.0 mg of the compound of Formula 2 was dissolved in a mixed solution of 7.2 mL of vinyl butanoate and 0.8 mL of acetone, 50 mg of the same immobilized enzyme as that prepared in Example 19 was added, and an enzymatic reaction was carried out by stirring using a stirrer (600 rpm) at 25° C. for 15 hours. After the reaction was completed, the reaction mixture was filtered using an Ekicrodisc 25CR so as to remove the immobilized enzyme and then purified by flash silica gel column chromatography (eluent: n-hexane/ethyl acetate), thus giving 171.7 mg of a compound of Formula 3-5 as a colorless solid (optical purity 89.86% e.e.).

In addition, the state of the starting material compound of Formula 2 and formation of the target compound of Formula 3-5 and its enantiomer, a compound of Formula 3-5', were confirmed by the TLC method and the HPLC method below.

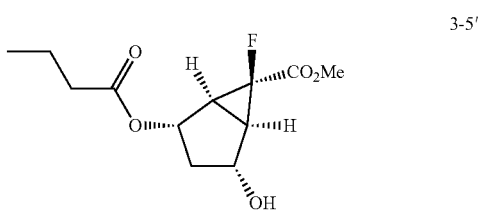 [SMILES: CCCC(=O)O[C@H]1C[C@@H](O)[C@H]2[C@@H]1[C@]2(F)C(=O)OC]

3-5'

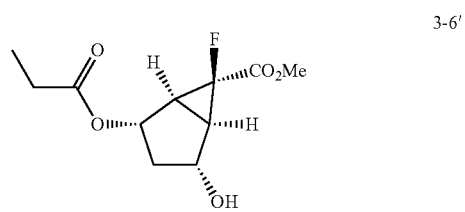 [SMILES: CCC(=O)O[C@H]1C[C@@H](O)[C@H]2[C@@H]1[C@]2(F)C(=O)OC]

3-6'

(TLC method: TLC plate; silica gel Si60 (Art 1.5715, Merck & Co., Inc.))
Developing solvent; n-hexane/ethyl acetate ~10/1
Coloration; anisaldehyde/conc. sulfuric acid/acetic acid=1/2/100
Rf value; compound of Formula 2=0.20, compound of Formula 3-5=0.55
(HPLC method: column CHIRALCEL OJ-RH 4.6 mm ID×150 mm L (Daicel Chemical Industries, Ltd.))
Mobile phase; (methanol:acetonitrile=1:1)/0.1% phosphoric acid aqueous solution=52/48
Flow rate; 0.8 mL/min
Temperature; 35° C.
Detection; UV 195 nm
Retention time;
compound of Formula 3-5: 4.2 min
compound of Formula 3-5': 4.5 min

Example 25

Vinyl Propionate Reaction

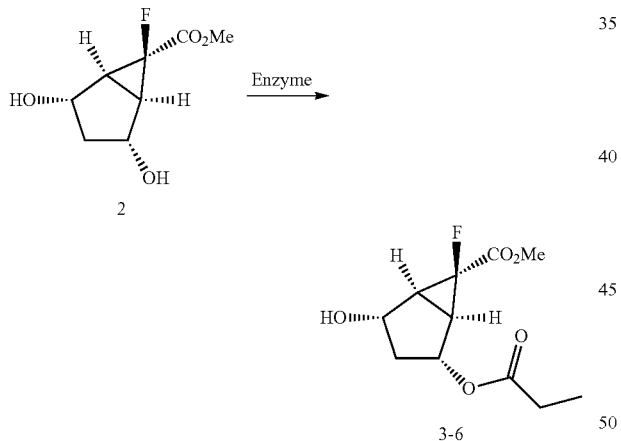

202.4 mg of the compound of Formula 2 was dissolved in a mixed solution of 7.2 mL of vinyl propionate and 0.8 mL of acetone, 50 mg of the same immobilized enzyme as that prepared in Example 19 was added, and an enzymatic reaction was carried out by stirring using a stirrer (600 rpm) at 25° C. for 15 hours. After the reaction was completed, the reaction mixture was filtered using an Ekicrodisc 25CR so as to remove the immobilized enzyme and then purified by flash silica gel column chromatography (eluent: n-hexane/ethyl acetate), thus giving 194.4 mg of a compound of Formula 3-6 as a colorless solid (optical purity 99.99% e.e.).

In addition, the state of the starting material compound of Formula 2 and formation of the target compound of Formula 3-6 and its enantiomer, a compound of Formula 3-6', were confirmed by the TLC method and the HPLC method below.

(TLC method: TLC plate; silica gel Si60 (Art 1.5715, Merck & Co., Inc.))
Developing solvent; n-hexane/ethyl acetate=10/1
Coloration; anisaldehyde/conc. sulfuric acid/acetic acid=1/2/100
Rf value; compound of Formula 2=0.20, compound of Formula 3-6=0.50
(HPLC method: column CHIRALCEL OJ-RH 4.6 mm ID×150 mm L (Daicel Chemical Industries, Ltd.))
Mobile phase; methanol/0.1% phosphoric acid aqueous solution=44/56
Flow rate; 0.8 mL/min
Temperature; 35° C.
Detection; UV 195 nm
Retention time;
compound of Formula 3-6: 18.1 min
compound of Formula 3-6'; 15.0 min

Example 26

Synthesis 1 from Diacetyl Compound

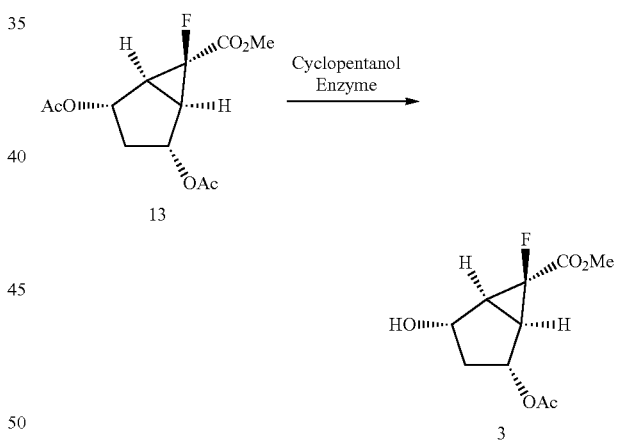

50 mg of a compound of Formula 13 and 50 mg of each of the enzymes shown in Table 9 were added to 2.0 mL of a mixture of isopropyl ether and 0.05 mL of cyclopentanol, which is an acyl group acceptor, and stirred using a stirrer (600 rpm) at room temperature (24° C.) for 94 hours. The compound of Formula 13 was produced by a method shown in Reference Example 2, which is described later.

Among the enzymes shown in Table 9, with regard to Lipase AK "Amano" 20, Lipase PS "Amano" SD, CHE "Amano" 2, and Lipase AS "Amano", commercial products were used. Furthermore, with regard to Lipase QUI, Lipase PS "Amano" SD, Lipase AK "Amano" 20, Lipase R "Amano", Lipase AY "Amano" 30G, and Lipase TL, commercial products were immobilized on Toyonite 200M or Toyonite 200P by the same method as in Example 14 and used. Moreover, with regard to a *Dipodascus australiensis* NBRC10805 microorganism culture fluid supernatant-derived enzyme, it was immobilized on Toyonite 200M by the method described in Example 18 and used.

After the reaction was completed, the enzyme was removed by filtration using an Ekicrodisc 25CR, and the solution was dried under reduced pressure, dissolved in 1 mL of methanol, and then subjected to analysis by the above-mentioned HPLC method for the compound of Formula 3.

Table 9 shows the amounts formed and optical purities of the compound of Formula 3 after carrying out a reaction using each of the enzymes.

TABLE 9

| Enzyme name (trade name) | Derived from | Support for immobilization | Amount of 3 formed | Optical purity of 3 |
|---|---|---|---|---|
| Lipase QLM | *Alcaligenes* sp. | Toyonite 200M | 8.49 mg | >99% e.e. |
| Lipase PS "Amano" SD | *Burkholderia cepacia* | Toyonite 200M | 2.21 mg | >99% e.e. |
| Lipase AK "Amano" 20 | *Pseudomonas fluorescens* | Toyonite 200M | 1.56 mg | >99% e.e. |
| Lipase AK "Amano" 20 | *Pseudomonas fluorescens* | None | 0.94 mg | >99% e.e. |
| Lipase PS "Amano" SD | *Burkholderia cepacia* | None | 0.41 mg | >99% e.e. |
| Lipase R "Amano" | *Penicillium roqueforti* | Toyonite 200M | 0.38 mg | >99% e.e. |
| CHE "Amano" 2 | *Pseudomonas* sp. | None | 0.30 mg | >99% e.e. |
| NBRC10805/200M (prepared in the present invention) | *Dipodascus australiensis* NBRC10805 | Toyonite 200M | 0.12 mg | >99% e.e. |
| Lipase AY "Amano" 30G | *Candida rugosa* | Toyonite 200M | 6.46 mg | 88.56% e.e. |
| Lipase TL | *Pseudomonas stutzeri* | Toyonite 200M | 2.94 mg | 80.72% e.e. |
| Lipase AS "Amano" | *Aspergillus niger* | None | 0.23 mg | 72.49% e.e. |
| Lipase AY "Amano" 30G | *Candida rugosa* | Toyonite 200P | 7.13 mg | 70.59% e.e. |

Example 27

Synthesis 2 of Sample from Diacetyl Compound

The enzymatic reactions below were carried out using Lipase QLM, Lipase OF, Lipase PL, and Novozym CALAL immobilized enzymes as the enzymes used.

0.05 mL of the acyl group acceptor cyclopentanol with toluene added to give 2.0 mL, 0.05 mL of the acyl group acceptor cyclopentanol with isopropyl ether added to give 2.0 mL, 0.05 mL of the acyl group acceptor 2-butanol with toluene added to give 2.0 mL, 0.05 mL of the acyl group acceptor 2-butanol with isopropyl ether added to give 2.0 mL, 0.05 mL of the acyl group acceptor 2-propanol with toluene added to give 2.0 mL, and 0.05 mL of the acyl group acceptor 2-propanol with isopropyl ether added to give 2.0 mL were prepared, and 50 mg of each of the enzymes shown in Table 10 and 50 mg of the compound of Formula 13 were added to each of the above and stirred using a stirrer (600 rpm) at room temperature (21° C. to 24° C.) for 19 hours. After the reaction was completed, the immobilized enzyme was removed by filtration using an Ekicrodisc 25CR, and the solution was dried under reduced pressure, dissolved in 1 mL of methanol, and then subjected to analysis by the above-mentioned HPLC method for the compound of Formula 3.

Table 10 shows the amounts formed and optical purities of the compound of Formula 3 after the reactions were carried out using each of the enzymes.

TABLE 10

| Enzyme/support for immobilization | Reaction solvent | Amount of 3 formed | Optical purity of 3 |
|---|---|---|---|
| Lipase OF/Toyonite 200P | Toluene/2-Propanol | 0.09 mg | >99% e.e. |
| Lipase OF/Toyonite 200P | Isopropyl ether/2-Propanol | 0 mg | |
| Lipase OF/Toyonite 200P | Toluene/2-Butanol | 0.12 mg | >99% e.e. |
| Lipase OF/Toyonite 200P | Isopropyl ether/2-Butanol | 0 mg | |
| Lipase OF/Toyonite 200P | Toluene/cyclopentanol | 0.64 mg | >99% e.e. |
| Lipase OF/Toyonite 200P | Isopropyl ether/cyclopentanol | 0 mg | |
| Lipase QLM/Toyonite 200M | Toluene/2-Propanol | 2.91 mg | 7.46% e.e. |
| Lipase QLM/Toyonite 200M | Isopropyl ether/2-Propanol | 2.13 mg | 61.63% e.e. |
| Lipase QLM/Toyonite 200M | Toluene/2-Butanol | 0.58 mg | 47.85% e.e. |
| Lipase QLM/Toyonite 200M | Isopropyl ether/2-Butanol | 3.39 mg | 51.69% e.e. |
| Lipase QLM/Toyonite 200M | Toluene/cyclopentanol | 2.97 mg | 6.21% e.e. |
| Lipase QLM/Toyonite 200M | Isopropyl ether/cyclopentanol | 2.15 mg | 93.09% e.e. |
| Novozym CALAL/Toyonite 200M | Toluene/2-Propanol | 0 mg | |
| Novozym CALAL/Toyonite 200M | Isopropyl ether/2-Propanol | 0.08 mg | 52.11% e.e. |
| Novozym CALAL/Toyonite 200M | Toluene/2-Butanol | 0 mg | |
| Novozym CALAL/Toyonite 200M | Isopropyl ether/2-Butanol | 0.15 mg | 42.45% e.e. |

TABLE 10-continued

| Enzyme/support for immobilization | Reaction solvent | Amount of 3 formed | Optical purity of 3 |
|---|---|---|---|
| Novozym CALAL/Toyonite 200M | Toluene/cyclopentanol | 0 mg | |
| Novozym CALAL/Toyonite 200M | Isopropyl ether/cyclopsntanol | 0 mg | |
| Lipase PL/Toyonite 200M | Toluene/2-Propancl | 0 mg | |
| Lipase PL/Toyonite 200M | Isopropyl ether/2-Propanol | 0 mg | |
| Lipase PL/Toyonite 200M | Toluene/2-Butanol | 0 mg | |
| Lipase PL/Toyonite 200M | Igopropyl ether/2-Butanol | 0 mg | |
| Lipase PL/Toyonite 200M | Toluene/cyclopentanol | 0 mg | |
| Lipase PL/Toyonite 200M | Isopropyl ether/cyclopentariol | 0 mg | |

Example 28

Mixture of dimethyl fluoro[(1R,5R)-5-hydroxycyclopent-2-en-1-yl]propanedioate (10a) and dimethyl fluoro[(1S,5S)-5-hydroxycyclopent-2-en-1-yl]propanedioate (10b)

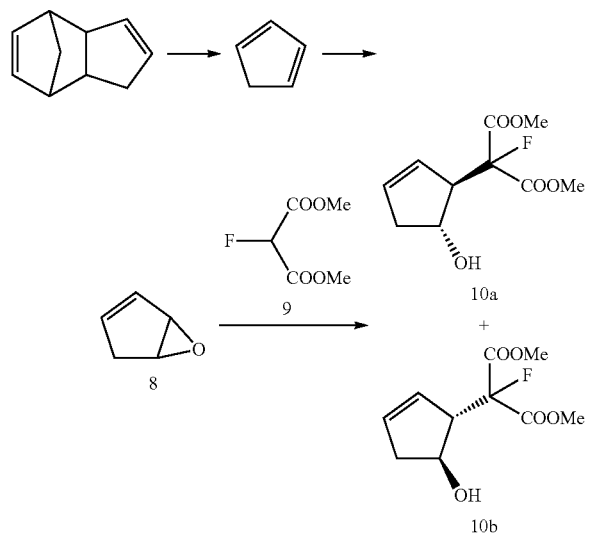 [SMILES: C1=CC2C3C=CC(C3)C2C1 ; C1=CCC=C1 ; COC(=O)C(F)C(=O)OC ; COC(=O)C(F)(C(=O)OC)[C@@H]1C=CC[C@H]1O ; C1=CC2OC2C1 ; COC(=O)C(F)(C(=O)OC)[C@H]1C=CC[C@@H]1O]

Dicyclopentadiene was placed in a recovery flask and immersed in an oil bath set at 185° C. to 190° C. A component distilling at 39° C. to 41° C. was collected (trapped in a dry ice-acetone bath), thus giving cyclopentadiene as a colorless oily material 55.75 g (0.526 mol) of sodium carbonate was added to a dichloromethane (170 mL) solution of 19.041 g (0.288 mol) of the cyclopentadiene thus obtained, and cooling to −15° C. was carried out. 28.10 g (0.144 mol) of peroxyacetic acid (content 38.9%) was added thereto while keeping the internal temperature between −15° C. and −10° C. After stirring at −15° C. for 3.5 hours, 16.80 g (0.086 mol) of peroxyacetic acid was further added, stirring was carried out at −15° C. for 15 hours and at room temperature for 4.5 hours, and solids were then removed by filtration. The filtrate was dried with 10 g of magnesium sulfate, thus giving 250.63 g of a dichloromethane solution of 6-oxabicyclo[3.1.0]hex-2-ene (8).

52.170 g (0.241 mol) of a 25 w/w % methanol solution of sodium methoxide was added to a methanol (120 mL) solution of 39.99 g (0.266 mol) of dimethyl fluoropropanedioate (9) over 5 minutes while keeping the internal temperature between 20° C. and 30° C. After the solution thus obtained was stirred for 20 minutes, 200.432 g (0.117 mol) of the dichloromethane solution of the compound of Formula 8 was added thereto over 8 minutes while keeping the internal temperature between 25° C. and 35° C. After stirring at room temperature for 17 hours, 153 mL of a saturated ammonium chloride aqueous solution was added. 29 g of a 10% sodium thiosulfate aqueous solution was added, and the mixture was stirred and then separated. Extraction was carried out with 30 mL of dichloromethane, and the organic layers were combined and washed with 50 mL of saturated brine. After drying with magnesium sulfate concentration under reduced pressure was carried out. The concentrated residue was purified by flash silica gel column chromatography (eluent; n-hexane/ethyl acetate), thus giving 17.582 g of a mixture of the compound of Formula 10a and the compound of Formula 10b as a yellow oily material.

$^1$H NMR (300 MHz, CDCl$_3$: δ 2.32-2.39 (m, 1H), 2.45 (d, J=3.9 Hz, 1H), 2.75-2.84 (m, 1H), 3.47-3.58 (m, 1H), 3.87 (s, 6H), 4.54-4.60 (m, 1H), 5.46-5.49 (m, 1H), 5.87-5.89 (m, 1H).

Example 29

Methyl (1R,2R,4S,5S,6R)-6-fluoro-2,4-dihydroxybicyclo[3.1.0]hexane-6-carboxylate (2)

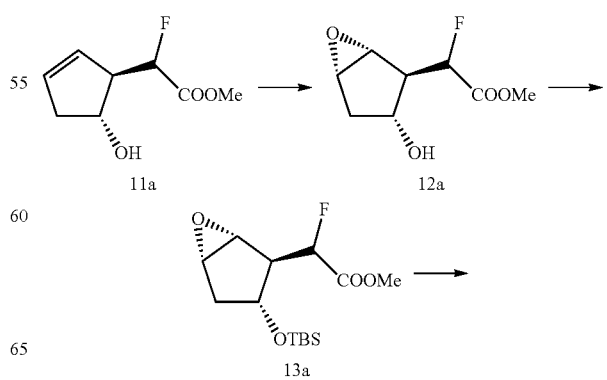

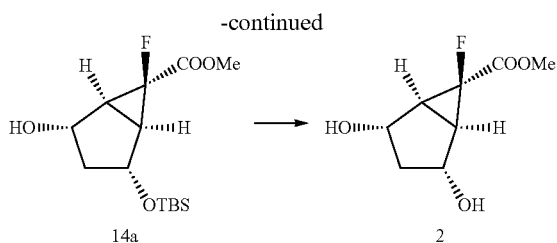

0.914 g (3.447 mmol) of vanadyl acetylacetonate (VO(acac)$_2$) was added to a chlorobenzene (143.70 g) solution of 30.00 g (172.25 mmol) of the compound of Formula 11a at room temperature. The mixture was heated to 60° C., and 44.91 g (348.03 mmol) of a 70% toluene solution of tert-butyl hydroperoxide (tBuOOH) was added thereto over 25 minutes while keeping the internal temperature between 55° C. and 60° C. The mixture was stirred at 55° C. for 5 hours and allowed to cool to room temperature. After adding 73.65 g of a 20% sodium thiosulfate aqueous solution and stirring for 30 minutes, extraction was carried out with 133 mL of ethyl acetate twice, The organic layers were combined, washed with saturated brine, and then concentrated under reduced pressure, thus giving 47.71 g of the compound of Formula 12a as a yellow oily material.

23.193 g (340.67 mmol) of imidazole and 32.682 g (216.82 mmol) of tert-butyldimethylsilyl chloride (TBSCl) were added to a DMF (63 mL) solution of the compound of Formula 12a thus obtained and stirring at room temperature was carried out for 2.5 hours. 170 mL of toluene and 150 mL of water were added thereto, and the mixture was stirred for 10 minutes and then separated. Extraction was carried out with 136 mL of toluene and the organic layers were combined, washed with 30 mL of water, and then concentrated under reduced pressure, thus giving 55.91 g of methyl [(1R,2R,3R,5S)-3-{[tert-butyl(dimethyl)silyl]oxy}-6-oxabicyc lo[3.1.0]hex-2-yl](fluoro)acetate (13a) as a brown oily material.

A THF (270 mL) solution of the compound of Formula 13a thus obtained was cooled to −50° C., and 210 mL (197.40 mmol) of a 0.94 mol/L triethylaluminum hexane solution was added thereto over 30 minutes while keeping the internal temperature between −55° C. and −50° C. After stirring at −50° C. for 30 minutes, 143 mL (228.80 mmol) of a 1.6 mol/L lithium hexamethyldisilazide (LiHMDS) hexane solution was added thereto over 10 minutes while keeping the internal temperature between −50° C. and −40° C. After stirring at −50° C. for 2 hours the reaction mixture was added over 20 minutes to 265.08 g of a 25% citric acid aqueous solution cooled at 5° C. 270 mL of ethyl acetate was added to the reaction mixture, which was stirred and then separated. Extraction was carried out with 100 mL of ethyl acetate, the organic layers were combined, washed with 50 mL of water, and then concentrated under reduced pressure, thus giving 56.65 g of methyl (1R,2R,4S,5S,6R)-2-[(tert-butyl(dimethyl) silyl]oxy)-6-fluoro-4-hydroxybicyclo[3.1.0]hexane-6-carboxylate (14a) as a brown oily material.

An acetonitrile (185 mL) solution of the compound of Formula 14a thus obtained was cooled to 0° C., and 30 mL of 1 N hydrochloric acid was added. After stirring at room temperature for 4.5 hours, a 4% sodium hydrogen carbonate aqueous solution (95.845 g) and 450 mL of ethyl acetate were added. The mixture was stirred for 10 minutes and then separated. Extraction was carried out with 400 mL of ethyl acetate three times, and the organic layers were then combined, dried with sodium sulfate, and concentrated under reduced pressure. The concentrated residue was precipitated from a mixed liquid of 108.58 g of ethyl acetate and 2.722 g of water, thus giving 21.34 g of the compound of Formula 2 as colorless crystals.

$^1$H NMR (500 MHz, DMSO-d$_6$): δ 1.66 (dd, J=4.6, 14.8 Hz, 1H): 1.97 (m, 1H), 2.17 (e, 2H), 3.72 (s, 3H), 4.18 (t, J=5.4 Hz, 2H), 4.93 (d, J=5.0 Hz, 2H). MS m/z: 213.1 [M+Na]$^+$. IR (KBr): 3548, 3413, 3295, 3239, 2922, 2751, 1732, 1616, 1467, 1442, 1381, 1336, 1285, 1265, 1235, 1198, 1181, 1130, 1078, 1041, 994, 947, 890, 805, 777, 733, 646, 566, 540, 480, 446 cm$^{-1}$. Anal. Calcd for C$_8$H$_{11}$FO$_4$H$_2$O: C, 46.15; H, 6.29; F, 9.13. Found: C, 46.11; H, 6.18; F, 9.09.

Reference Example 1

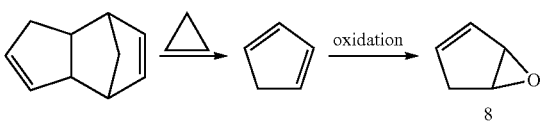

6-Oxabicyclo[3.1.0]hex-2-one (8)

A recovery flask was charged with 84.37 g (638.2 mmol) of dicyclopentadiene and immersed in an oil bath set at 185° C. to 190° C. A component distilling at 39° C. to 41° C. was collected (trapped by a dry ice-acetone bath), thus giving 73.2 g of cyclopentadiene as a colorless oily material. 176.0 g (1.66 mol) of sodium carbonate was placed in a dichloromethane (732 ml) solution of 73.2 g (1.107 mol) of the cyclopentadiene thus obtained, and the mixture was immersed in an ice bath. 198.5 g (886 mmol) of metachloroperoxybenzoic acid (content 77%) was added thereto portionwise over 30 minutes while keeping the internal temperature between 3° C. and 35° C. After stirring at room temperature for 15 hours, solids were removed by filtration (washed with 532 mL of dichloromethane). After most of the dichloromethane in the washings was removed by evaporation under reduced pressure, distillation was carried out under reduced pressure, thus giving 14.08 g of epoxide 8 as a pale yellow oily material. The results of $^1$H NMR measurement (300 MHz, DMSO-d$_6$) of epoxide 8 coincided with those described in the literature (Org. Lett., 7, 4573 (2005)).

$^1$H NMR (300 MHz, DMSO-d$_6$); δ 2.30-2.39 (m, 1H), 2.45-2.53 (m, 1H), 3.80-3.83 (m, 1H), 3.88-3.90 (m, 1H), 5.94-5.98 (m, 1H), 6.12-6.16 (m, 1H).

Reference Example 2

Preparation of Diacetyl Compound

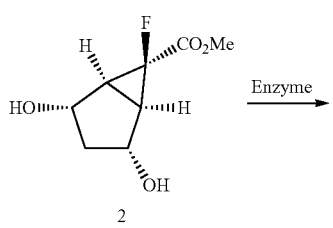

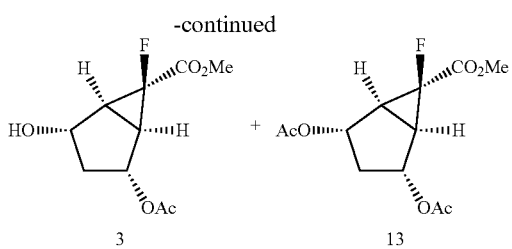

When preparing the compound of Formula 3 from the compound of Formula 2 by the enzymatic reactions shown in Examples 12 to 19, the diacetyl compound of Formula 13 is formed as a by-product in some cases. The amount of by-product produced can be regulated by controlling the speed at which a solution of the compound of Formula 2 is fed to a column-packed immobilized enzyme. For example, in Example 19, the yield of formation of the diacetyl compound was 3.8% (4.35 g). In this example, examination was carried out for the purpose of isolating the by-product.

Firstly, an immobilized enzyme was prepared using NOVOZYM 735 and Toyonite 200M by the same method as in Example 17, and a 6 mL volume column (Bond Elut Reservoir with frit: purchased from GL Sciences Inc.) was charged with 4.0 g of the immobilized enzyme thus obtained.

Subsequently, 18.28 g of crystals of the compound of Formula 2 was dissolved in 804 mL of vinyl acetate/acetone (10:1), and the solution was fed to the column charged with the above immobilized enzyme via a silicone tube using a peristaltic pump (Atto Corporation). The feed rate was 129 mL/hr. After feeding was completed, the discharged liquid was analyzed by the TLC method and the HPLC method, and from the results 19.02 g (yield 86.56%) of the compound of Formula 3 was obtained at an optical purity of 96.01% e.e. and 2.81 g (yield 10.9%) of the diacetyl compound of Formula 13 was obtained. The compound of Formula 3 and the diacetyl compound of Formula 13 could be separated by concentrating under reduced pressure the liquid discharged from the enzymatic reaction and then purifying the concentrated residue by flash silica gel column chromatography (eluent: n-hexane/ethyl acetate). After the diacetyl compound of Formula 13 was dissolved in ethyl acetate, it was recrystallized, thus giving it as a colorless solid.

$^1$H NMR (500 MHz, CDC1); δ 2.02 (dd, J=5.0, 16.5 Hz, 1H), 2.11 (s, 6H), 2.35 (ddd, J=7.0, 16.5 Hz, 1H), 2.45 (s, 2H), 3.81 (s, 3H), 5.27 (d, J=6.5 Hz 1H). $^{13}$C NMR (125 MHz, CDCl$_3$); δ 21.14, 35.27 (d, J=9.9 Hz), 39.99 (d, J=8.7 Hz), 52.99, 74.72, 76.74, 168.12, 168.31, 170.34, MS (Shimadzu LCMS-210EV ESI/APCI Dual positive) m/z: [M+Na]$^+$ 297.0

The abbreviations below are used throughout the specification.
Me: methyl
Et: ethyl
Ac; acetyl
Ph: phenyl
THF: tetrahydrofuran
TEMPO: 2,2,6,6-tetramethylpiperidine 1-oxyl
TMS: trimethylsilyl
DMSO: dimethyl sulfoxide
TfOH: trifluoromethanesulfonic acid
TMSOTf: trimethylsilyl trifluoromethanesulfonate
LiHMDS: lithium hexamethyldisilazide
HPLC: high-performance liquid chromatography
NMR: nuclear magnetic resonance
TLC: thin-layer chromatography The production method of the present invention can be applied in order to mass produce a bicyclo[3.1.0]hexane derivative, which is useful as a metabotropic glutamate receptor modulator.

What is claimed is:

1. A method for producing a bicyclo[3.1.0]hexane derivative represented by Formula (I) and a salt thereof

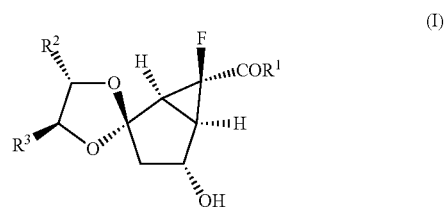

(in Formula (I), R$^1$ is
(1) —OH,
(2) —O—R$^a$, or
(3) —NR$^b$R$^c$,

R$^a$ is a C$_{1-6}$ alkyl group or a C$_{3-8}$ cycloalkyl group (said C$_{1-6}$ alkyl group or C$_{3-8}$ cycloalkyl group being unsubstituted or substituted with one or more C$_{1-6}$ alkoxy groups, hydroxy groups, halogens, aryl groups, or heteroaryl groups), R$^b$ and R$^c$ are identical or different and are each hydrogen, a halogen, a C$_{1-6}$ alkyl group, or a C$_{3-8}$ cycloalkyl group (said C$_{1-6}$ alkyl group or C$_{3-8}$ cycloalkyl group being unsubstituted or substituted with one or more hydroxy groups, C$_{1-6}$ alkoxy groups, aryl groups, or heteroaryl groups), or R$^b$ and R$^c$ are bonded to each other and, together with the adjacent nitrogen atom, form a 4- to 7-membered saturated heterocycle (said saturated heterocycle being unsubstituted or substituted with a hydroxy group, a C$_{1-6}$ alkyl group, or a C$_{1-6}$ alkoxy group), R$^2$ and R$^3$ are identical or different and are each hydrogen, a C$_{1-6}$ alkyl group, a C$_{3-8}$ cycloalkyl group, or a —(CH$_2$)$_m$-phenyl group, and m is 0, 1, or 2), said method comprising:

(A) converting a compound represented by Formula (II) into a compound represented by Formula (III), wherein the compound represented by Formula (III) is produced by reacting the compound represented by Formula (II) with an acyl group donor in the presence of a microorganism-derived enzyme

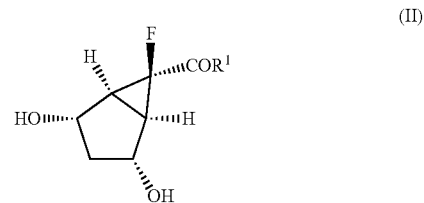

(R$^1$ in Formula (II) is as defined in Formula (I))

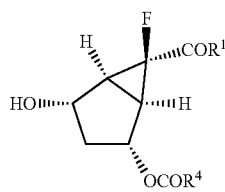

(III)

(in Formula (III), $R^1$ is as defined in Formula (I),
$R^4$ is hydrogen, a $C_{1-6}$ alkyl group, a $C_{3-8}$ cycloalkyl group, or a —$(CH_2)_n$-phenyl group (said $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups), and
n is 0, 1, or 2);
(B) converting said compound represented by Formula (III) into a compound represented by Formula (IV)

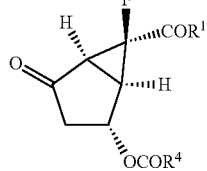

(IV)

($R^1$ and $R^4$ in Formula (IV) are as defined in Formula (I) and Formula (III));
(C) reacting said compound represented by Formula (IV) with a compound represented by Formula (V) to obtain a compound represented by Formula (VI)

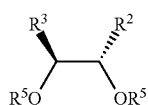

(V)

(in Formula (V), $R^2$ and $R^3$ are as defined in Formula (I), $R^5$ is hydrogen or Si—$(R^6)(R^7)(R^8)$, and
$R^6$, $R^7$ and $R^8$ are identical or different and are each a $C_{1-6}$ alkyl group or a phenyl group)

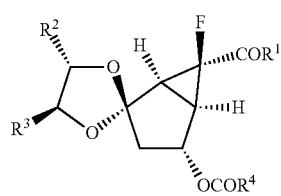

(VI)

($R^1$, $R^2$, and $R^3$ in Formula (VI) are as defined in Formula (I) and $R^4$ is as defined in Formula (III)), and (D) converting said compound represented by Formula (VI) into the compound represented by Formula (I).

2. A method for producing a compound represented by Formula (III) and a salt thereof

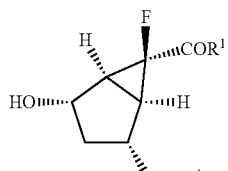

(III)

(in Formula (III), $R^1$ is
(1) —OH,
(2) —O—$R^a$, or
(3) —$NR^bR^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups),
or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group),
$R^4$ is hydrogen, a $C_{1-6}$ alkyl group, a $C_{3-8}$ cycloalkyl group, or a —$(CH_2)_n$-phenyl group (said $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups), and
n is 0, 1, or 2), said method comprising:
converting a compound represented by Formula (II) into the compound represented by Formula (III), wherein the compound represented by Formula (III) is produced by reacting the compound represented by Formula (II) with an acyl group donor in the presence of a microorganism-derived enzyme

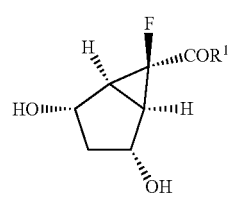

(II)

(R1 in Formula (II) is as defined in Formula (III)).
3. A method for producing a compound represented by Formula (VII) and a salt thereof

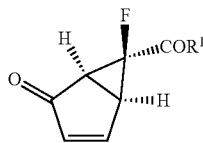

(VII)

(in Formula (VII), $R^1$ is
(1) —OH,
(2) —O—$R^a$, or
(3) —$NR^bR^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups),
or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group)), said method comprising:
(A) converting a compound represented by Formula (II) into a compound represented by Formula (III), wherein the compound represented by Formula (III) is produced by reacting the compound represented by Formula (II) with an acyl group donor in the presence of a microorganism-derived enzyme

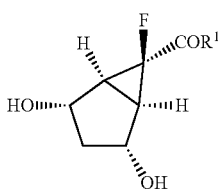

(II)

($R^1$ in Formula (II) is as defined in Formula (VII))

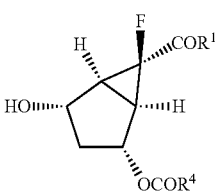

(III)

(in Formula (III), $R^1$ is as defined in Formula (VII),
$R^4$ is hydrogen, a $C_{1-6}$ alkyl group, a $C_{3-8}$ cycloalkyl group, or a —$(CH_2)_n$-phenyl group (said $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups), and
n is 0, 1, or 2);

(B) converting said compound represented by Formula (III) into a compound represented by Formula (IV)

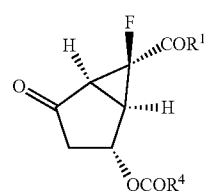

(IV)

($R^1$ and $R^4$ in Formula (IV) are as defined in Formula (VII) and Formula (III)); and
(C) converting said compound represented by Formula (IV) into the compound represented by Formula (VII).

4. The production method as set forth in claim 1, wherein $R^2$ and $R^3$ are identical or different and are each a phenyl group or a methyl group.

5. The production method as set forth in claim 1, wherein $R^5$ is hydrogen or a trimethylsilyl group.

6. The production method as set forth in claim 1, wherein $R^1$ is a methoxy group or an ethoxy group.

7. The production method as set forth in claim 1, wherein $R^4$ is a methyl group.

8. The production method as set forth in claim 1, wherein said microorganism is at least one type selected from the group consisting of the *Candida* genus, the *Aspergillus* genus, the *Thermomyces* genus, the *Penicillium* genus, the *Humicola* genus, the *Geotrichum* genus, the *Galactomyces* genus, and the *Burkholderia* genus.

9. The production method as set forth in claim 1, wherein said microorganism-derived enzyme is a lipase or an acylase.

10. The production method as set forth in claim 1, wherein said microorganism-derived enzyme is a *Candida Antarctica*-derived lipase A.

11. The production method as set forth in claim 1, wherein said enzyme is immobilized on a support.

12. The production method as set forth in claim 1, wherein said acyl group donor is vinyl acetate.

13. A method for producing a compound represented by Formula (II) and a salt thereof

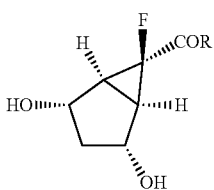

(II)

(in Formula (II), $R^1$ is
(1) —OH,
(2) —O—$R^a$, or
(3) —$NR^bR^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups), or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group)), said method comprising:

(A) reacting a compound represented by Formula (VIII) with a compound represented by Formula (IX) to obtain a mixture formed from a compound represented by Formula (Xa) and a compound represented by Formula (Xb)

(VIII)

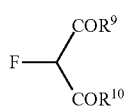

(IX)

(in Formula (IX), $R^9$ and $R^{10}$ are identical or different and are each
(1) —OH,
(2) —O—$R^a$, or
(3) —$NR^bR^c$, $R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups), $R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups), or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group))

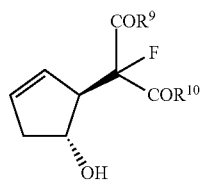

(Xa)

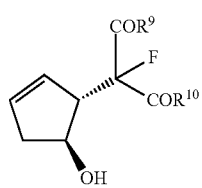

(Xb)

($R^9$ and $R^{10}$ in Formulae (Xa) and (Xb) are as defined in Formula (IX));

(B) converting the mixture formed from said compound represented by Formula (Xa) and said compound represented by Formula (Xb) into a mixture formed from a compound represented by Formula (XIa) and a compound represented by Formula (XIb)

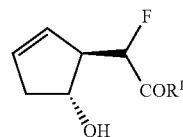

(XIa)

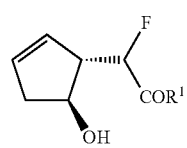

(XIb)

($R^1$ in Formulae (XIa) and (XIb) is as defined in Formula (II));

(C) converting the mixture formed from said compound represented by Formula (XIa) and said compound represented by Formula (XIb) into a mixture formed from a compound represented by Formula (XIIa) and a compound represented by Formula (XIIb)

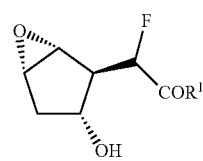

(XIIa)

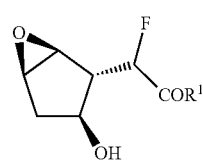

(XIIb)

($R^1$ in Formulae (XIIa) and (XIIb) is as defined in Formula (II)); and (D) converting the mixture formed from said compound represented by Formula (XIIa) and said compound represented by Formula (XIIb) into the compound represented by Formula (II).

14. A method for producing a mixture formed from a compound represented by Formula (Xa) and a compound represented by Formula (Xb) and salts thereof

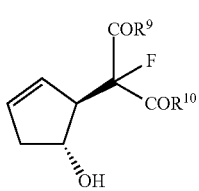

(Xa)

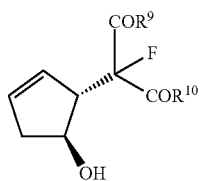

(in Formulae (Xa) and (Xb), $R^9$ and $R^{10}$ are identical or different and are each
(1) —OH,
(2) —O—$R^a$, or
(3) —N$R^b R^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups),
or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group)), said method comprising:
reacting a compound represented by Formula (VIII) with a compound represented by Formula (IX) so as to convert them into a mixture formed from said compound represented by Formula (Xa) and said compound represented by Formula (Xb)

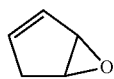

(VIII)

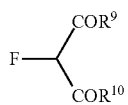

(IX)

($R^9$ and $R^{10}$ in Formula (IX) are as defined in Formula (Xa) and Formula (Xb)).

15. The production method as set forth in claim 13, wherein $R^1$, $R^9$, and $R^{10}$ are each a methoxy group or an ethoxy group.

16. A compound represented by Formula (VI) and a salt thereof

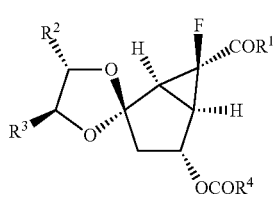

(VI)

(in Formula (VI), $R^1$ is
(1) —OH,
(2) —O—$R^a$, or
(3) —N$R^b R^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups),
or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group),
$R^2$ and $R^3$ are identical or different and are each hydrogen, a $C_{1-6}$ alkyl group, a $C_{3-8}$ cycloalkyl group, or a —(CH$_2$)$_m$-phenyl group,
m is 0, 1, or 2,
$R^4$ is hydrogen, a $C_{1-6}$ alkyl group, a $C_{3-8}$ cycloalkyl group, or a —(CH$_2$)$_n$-phenyl group (said $C_{1-6}$ alkyl group, $C_{3-8}$ cycloalkyl group, or —(CH$_2$)$_n$-phenyl group being unsubstituted or substituted with one or more halogens, hydroxy groups, $C_{1-6}$ alkyl groups, or $C_{1-6}$ alkoxy groups), and
n is 0, 1, or 2).

17. A method for producing a compound represented by Formula (III) and a salt thereof

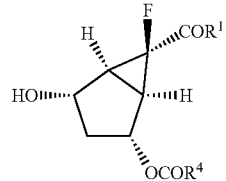

(III)

(in Formula (III), $R^1$ is
(1) —OH,
(2) —O—$R^a$, or
(3) —N$R^b R^c$,
$R^a$ is a $C_{1-6}$ alkyl group or a $C_{3-8}$ cycloalkyl group (said $C_{1-6}$ alkyl group or $C_{3-8}$ cycloalkyl group being unsubstituted or substituted with one or more $C_{1-6}$ alkoxy groups, hydroxy groups, halogens, aryl groups, or heteroaryl groups),
$R^b$ and $R^c$ are identical or different and are each hydrogen, a halogen, a $C_{1-6}$ alkyl group, or a $C_{3-8}$ cycloalkyl group (said $C_{1-6}$ alkyl group or $C_{3-8}$ cycloalkyl group being unsubstituted or substituted with one or more hydroxy groups, $C_{1-6}$ alkoxy groups, aryl groups, or heteroaryl groups),
or $R^b$ and $R^c$ are bonded to each other and, together with the adjacent nitrogen atom, form a 4- to 7-membered saturated heterocycle (said saturated heterocycle being unsubstituted or substituted with a hydroxy group, a $C_{1-6}$ alkyl group, or a $C_{1-6}$ alkoxy group),
$R^4$ is hydrogen, a $C_{1-6}$ alkyl group, a $C_{3-8}$ cycloalkyl group, or a —(CH$_2$)$_n$-phenyl group (said $C_{1-6}$ alkyl group, $C_{3-8}$ cycloalkyl group, or —(CH$_2$)$_n$-phenyl group being unsubstituted or substituted with one or more halogens, hydroxy groups, $C_{1-6}$ alkyl groups, or $C_{1-6}$ alkoxy groups), and n is 0, 1, or 2), said method comprising:

converting a compound represented by Formula (XIII) into said compound represented by Formula (III), wherein the compound represented by Formula (III) is produced by reacting the compound represented by Formula (XIII) with an acyl group acceptor in the presence of a microorganism-derived enzyme

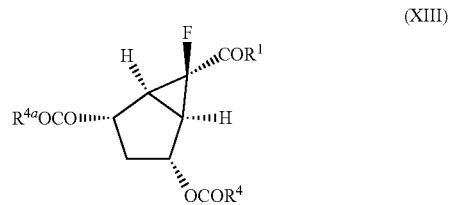

(XIII)

(in Formula (XIII), $R^4$ and $R^{4a}$ are identical or different and are each hydrogen, a $C_{1-6}$ alkyl group, a $C_{3-8}$ cycloalkyl group, or a —$(CH_2)_n$-phenyl group (said $C_{1-6}$ alkyl group, $C_{3-8}$ cycloalkyl group, or —$(CH_2)_n$-phenyl group being unsubstituted or substituted with one or more halogens, hydroxy groups, $C_{1-6}$ alkyl groups, or $C_{1-6}$ alkoxy groups) and n is 0, 1, or 2).

18. The production method as set forth in claim 17, wherein $R^1$ is a methoxy group or an ethoxy group, and $R^4$ and $R^{4a}$ are both methyl groups.

19. The production method as set forth in claim 17, wherein said microorganism is at least one type selected from the group consisting of the *Candida* genus, the *Aspergillus* genus, the *Alcaligenes* genus, the *Pseudomonas* genus, the *Dipodascus* genus, *Penicillium* genus, and the *Burkholderia* genus.

20. The production method as set forth in claim 17, wherein said microorganism-derived enzyme is a lipase or an esterase.

21. The production method as set forth in claim 17, wherein said microorganism-derived enzyme is a lipase derived from at least one type selected from the group consisting of *Alcaligenes* sp., *Burkholderia cepacia*, *Pseudomonas fluorescens*, and *Candida rugosa*.

22. The production method as set forth in claim 17, wherein said enzyme is immobilized on a support.

23. The production method as set forth in claim 17, wherein said acyl group acceptor is cyclopentanol.

\* \* \* \* \*